US011912823B2

(12) United States Patent
Vissvesvaran et al.

(10) Patent No.: US 11,912,823 B2
(45) Date of Patent: *Feb. 27, 2024

(54) METHODS OF PREPARING A POLOXAMER FOR USE IN CELL CULTURE MEDIUM

(71) Applicant: Genentech, Inc., South San Francisco, CA (US)

(72) Inventors: Ganesh Prasadh Vissvesvaran, South San Francisco, CA (US); Robert David Kiss, South San Francisco, CA (US); Steven J. Meier, South San Francisco, CA (US); Inchan Kwon, Charlottesville, VA (US); Kara Calhoun, South San Francisco, CA (US); Kate Winchester, South San Francisco, CA (US); Amelia Adams, South San Francisco, CA (US); Marion Glenn, South San Francisco, CA (US); Stefan Koenig, South San Francisco, CA (US); Alan Deese, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 295 days.

This patent is subject to a terminal disclaimer.

(21) Appl. No.: 17/319,886

(22) Filed: May 13, 2021

(65) Prior Publication Data

US 2021/0371587 A1 Dec. 2, 2021

Related U.S. Application Data

(60) Division of application No. 15/273,155, filed on Sep. 22, 2016, now Pat. No. 11,034,793, which is a continuation of application No. PCT/US2015/022592, filed on Mar. 25, 2015.

(60) Provisional application No. 61/970,281, filed on Mar. 25, 2014.

(51) Int. Cl.
*C08G 65/30* (2006.01)
*C12N 5/00* (2006.01)
*C07K 16/00* (2006.01)

(52) U.S. Cl.
CPC .............. *C08G 65/30* (2013.01); *C07K 16/00* (2013.01); *C12N 5/0018* (2013.01); *C07K 2317/14* (2013.01); *C08G 2650/50* (2013.01); *C12N 2500/50* (2013.01)

(58) Field of Classification Search
CPC .............. C08G 65/30; C08G 2650/50; C08G 2650/58; C08G 65/34; C08G 65/48; C07K 16/00; C07K 2317/14; C07K 1/02; C12N 5/0018; C12N 2500/50; C12N 5/00
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly |
| 4,927,762 A | 5/1990 | Darfler |
| 5,122,469 A | 6/1992 | Mather |
| 5,531,925 A | 7/1996 | Landh |
| 5,545,806 A | 8/1996 | Lonberg et al. |
| 5,545,807 A | 8/1996 | Surani |
| 5,569,825 A | 10/1996 | Lonberg |
| 5,625,126 A | 4/1997 | Lonberg |
| 5,631,144 A | 5/1997 | Lemoine |
| 5,633,425 A | 5/1997 | Lonberg et al. |
| 5,661,016 A | 8/1997 | Lonberg et al. |
| 5,804,420 A | 9/1998 | Chan |
| 5,912,228 A | 6/1999 | Lambert, Jr. |
| 5,959,177 A | 9/1999 | Hein |
| 6,040,498 A | 3/2000 | Stomp |
| 6,417,429 B1 | 7/2002 | Hein |
| 6,420,548 B1 | 7/2002 | Vezina |
| 7,125,978 B1 | 10/2006 | Vezina |
| 7,887,844 B2 | 2/2011 | Appel et al. |
| 11,034,793 B2 | 6/2021 | Vissvesvaran |
| 2005/0220831 A1 | 10/2005 | Jorsal |
| 2005/0227355 A1 | 10/2005 | Kjell |
| 2006/0115535 A1 | 6/2006 | Lisa et al. |
| 2009/0156482 A1 | 6/2009 | Jin et al. |
| 2011/0151506 A1 | 6/2011 | Calvosa et al. |

FOREIGN PATENT DOCUMENTS

| | | |
|---|---|---|
| CN | 101910408 A | 12/2010 |
| DE | 266710 A3 | 4/1989 |
| EP | 0183070 A2 | 6/1986 |
| EP | 0183070 A3 | 9/1987 |
| EP | 0244234 A2 | 11/1987 |

(Continued)

OTHER PUBLICATIONS

Almeida, H. et al. (2012). "Temperature and pH Stimuli-Responsive Polymers and Their Applications In Controlled and Self-Regulated Drug Delivery," Journal of Applied Pharmaceutical Science 2(6):1-10.

Barnes, D. et al. (Mar. 1, 1980). "Methods for Growth of Cultured Cells In Serum-Free Medium," Anal. Biochem. 102(2):255-270.

Brüggemann, M. et al. (1993). "Designer Mice: The Production of Human Antibody Repertoires in Transgenic Animals," Year in Immuno. 7:33-40.

Carter, P. et al. (Feb. 1992). "High Level *Escherichia coli* Expression and Production of a Bivalent Humanized Antibody Fragment," Bio/Technology 10:163-167.

Chisti, Y. (Oct. 2000). "Animal-Cell Damage in Sparged Bioreactors," Trends Biotechnol. 18(10):420-432.

(Continued)

*Primary Examiner* — Titilayo Moloye
(74) *Attorney, Agent, or Firm* — Morrison & Foerster LLP

(57) ABSTRACT

Provided herein are methods of preparing a poloxamer for use in a cell culture medium. Also provided herein are cell culture media containing the poloxamer prepared by the methods herein, as well as methods of using the media for cell culturing and polypeptide production from cells.

13 Claims, 11 Drawing Sheets

(56) References Cited

FOREIGN PATENT DOCUMENTS

| | | |
|---|---|---|
| EP | 0244234 A3 | 10/1988 |
| EP | 0402226 A1 | 12/1990 |
| EP | 0183070 B1 | 10/1991 |
| EP | 0244234 B2 | 11/2001 |
| EP | 0244234 B1 | 7/2003 |
| EP | 1661558 B1 | 7/2010 |
| JP | H04501660 A | 3/1992 |
| JP | H07502197 | 3/1995 |
| JP | H09508359 | 8/1997 |
| JP | 2006151980 A | 6/2006 |
| JP | 2006521425 A | 9/2006 |
| JP | 2007501115 A | 1/2007 |
| JP | 2010500411 A | 1/2010 |
| JP | 2010525137 A | 7/2010 |
| RU | 2222547 C2 | 1/2004 |
| WO | 198700195 A1 | 1/1987 |
| WO | 199003430 A1 | 4/1990 |
| WO | 199013646 A1 | 11/1990 |
| WO | 199110741 A1 | 7/1991 |
| WO | 199519180 A1 | 7/1995 |
| WO | 199633735 A1 | 10/1996 |
| WO | 199634096 A1 | 10/1996 |
| WO | 199824893 A2 | 6/1998 |
| WO | 199824893 A3 | 8/1998 |
| WO | 2004071452 A2 | 8/2004 |
| WO | 2004071452 A3 | 11/2004 |
| WO | 2005014162 A1 | 2/2005 |
| WO | 2006044738 A2 | 4/2006 |
| WO | 2006044738 A3 | 5/2007 |
| WO | 2008021347 A2 | 2/2008 |
| WO | 2008021347 A3 | 8/2008 |
| WO | 2008133422 A1 | 11/2008 |
| WO | 2009055312 A1 | 4/2009 |
| WO | 2009086309 A2 | 7/2009 |
| WO | 2009086309 A3 | 10/2009 |
| WO | 2013144341 A1 | 10/2013 |
| WO | 2013144341 A9 | 1/2014 |

OTHER PUBLICATIONS

Clackson, T. et al. (Aug. 15, 1991). "Making Antibody Fragments Using Phage Display Libraries," Nature 352:624-628.
Davies, J.T. (1957). "A Quantitative Kinetic Theory of Emulsion Type I. Physical Chemistry of The Emulsifying Agent," Gas/Liquid and Liquid/Liquid Interfaces: Proc. of 2nd Intl. Congress Surface Activity, Butterworths, London, pp. 426-438.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Final Office Action, dated Jul. 25, 2019, for U.S. Appl. No. 15/273,155, filed Sep. 22, 2016, 23 pages.
Final Office Action, dated Nov. 4, 2020, for U.S. Appl. No. 15/273,155, filed Sep. 22, 2016, 9 pages.
Fishwild, D.M. et al. (1996). "High-Avidity Human IgGx Monclonal Antibodies From a Novel Strain of Minilocus Transgenic Mice," Nature Biotechnology 14:845-851.
Gerngross, T.U. (Nov. 2004). "Advances in the Production of Human Therapeutic Proteins in Yeasts and Filamentous Fungi," Nature Biotechnology 22(11):1409-1414.
Graham, F.L. et al. (1977). "Characteristics Of A Human Cell Line Transformed By DNA From Human Adenovirus Type 5," Journal General Virology 36(1):59-74.
Griffin, W.C. (Jan. 1954). "Calculation of HLB Values of Non-Ionic Surfactants," J. Soc. Cosmet. Chemists 5(4):249-256.
Guss, B. et al. (Jul. 1986). "Structure of the IgG-Binding Regions of Streptococcal Protein G," EMBO J. 5(7):1567-1575.
Ham, R.J. et al. (1979). "Media and Growth Requirements," Meth. Enz. 58:44-93.
Hammerling, G.J. et al. (1981). "Production of Antibody-Producing Hybridomas in the Rodent Systems," in Research Monographs in Immunology, Elsevier/North-Holland Biomedical Press 3:563-587.
Harlow, E. et al. (1988) Antibodies: A Laboratory Manual, Cold Spring Harbor Laboratory pp. 53-137.
Hongo, J.A.S. et al. (1995). "Development and Characterization of Murine Monoclonal Antibodies to the Latency-Associated Peptide of Transforming Growth Factor β1," Hybridoma 14(3):253-260.
International Search Report dated Jun. 15, 2015, for PCT Application No. PCT/US2015/022592, filed on Mar. 25, 2015, 4 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Kabanov, A.V. et al. (1995) "Micelle Formation and Solubilization of Fluorescent Probes in Poly(oxyethylene-b-oxypropylene-b-oxyethylene) Solutions," Macromolecules 28(7):2303-2314.
Köhler, G. et al. (Aug. 7, 1975). "Continuous Cultures of Fused Cells Secreting Antibody of Predefined Specificity," Nature 256:495-497.
Lee, C.V. et al. (2004). "Bivalent Antibody Phage Display Mimics Natural Immunoglobulin," J. Immunol. Methods 284(1-2):119-132.
Lee, C.V. et al. (2004). "High-affinity Human Antibodies From Phage-displayed Synthetic Fab Libraries With a Single Framework Scaffold," J. Mol. Biol. 340(5):1073-1093.
Li, H. et al. (Feb. 2006, e-published on Jan. 22, 2006). "Optimization of Humanized IgGs in Glycoengineered Pichia Pastoris," Nature Biotechnology 24(2):210-215.
Lindmark, R. et al. (1983). "Binding of Immunoglobulins to Protein A and Immunoglobulin Levels in Mammalian Sera," J. Immunol. Meth. 62:1-13.
Lonberg, N. et al. (Apr. 28, 1994). "Antigen-Specific Human Antibodies From Mice Comprising Four Distinct Genetic Modifications," Nature 368:856-859.
Lonberg, N. et al. (1995). "Human Antibodies From Transgenic Mice," Intern. Rev. Immunol. 13:65-93.
Marks, J.D. et al. (1991). "By-Passing Immunization: Human Antibodies From V-Genen Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Mather, J.P. (Aug. 1980) "Establishment and Characterization of Two Distinct Mouse Testicular Epithelial Cell Lines," Biol. Reprod. 23(1):243-252.
Mather, J.P. et al. (1982). "Culture of Testicular Cells in Hormone-Supplemented Serum-Free Medium," Annals N.Y. Acad. Sci. 383:44-68.
Meier, S.J. et al. (Feb. 20, 1999) "Cell Death From Bursting Bubbles: Role of Cell Attachment to Rising Bubbles in Sparaged Reactors," Biotechnol. Bioeng. 62(4):468-478. Erratum, Biotechnol. Bioeng. 74(6):544-546, (Sep. 20, 2001).
Morrison, S.L. (Apr. 28, 1994). "Success in Specification," Nature 368:812-813.
Neuberger, M. (Jul. 1996). "Generating High-Avidity Human Mabs in Mice," Nature Biotechnology 14:826.
Non-Final Office Action, dated Jan. 8, 2019, for U.S. Appl. No. 15/273,155, filed Sep. 22, 2016, 23 pages.
Non-Final Office Action, dated May 8, 2020, for U.S. Appl. No. 15/273,155, filed Sep. 22, 2016, 16 pages.
Patkar, A. et al. (2002). "Flow Cytometry as a Useful Tool for Process Development: Rapid Evaluation of Expression Systems," Journal of Biotechnology 93:217-229.
Plückthun, A. (1994). "Antibodies from Escherichia coli," in Chapter 11 The Pharmacology of Monoclonal Antibodies, vol. 113, Rosenburg and Moore eds., Springer-Verlag, New York, pp. 269-315, 48 pages.
Shah, T.J. et al. (2007). "Process Optimization and Characterization of Poloxamer Solid Dispersions of a Poorly Water-soluble Drug," AAPS PharmSciTech, 8(2):Article 29, pp. E1-E7.
Sidhu, S.S. et al. (2004). "Phage-Displayed Antibody Libraries Synthetic Heavy Chain Complementarity Determining Regions," J. Mol. Biol. 338(2):299-310.

(56) References Cited

OTHER PUBLICATIONS

Tharmalingam, T. et al. (2008). "Pluronic Enhances the Robustness and Reduces the Cell Attachment of Mammalian Cells," Mol. Biotechnol. 39(2):167-177.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Vijayasankaran, N. et al. (2005; e-published on Dec. 30, 2004). "Synthesis of poly[® -3-hydroxybutyric Acid) in the Cytoplasm of Pichia Pastoris under Oxygen Limitation," Biomacromolecules 6(2):604:611.
Written Opinion dated Jun. 15, 2015, for PCT Application No. PCT/US2015/022592, filed on Mar. 25, 2015, 7 pages.
Yazaki, P.J. et al. (2003). "Expression of Recombinant Antibodies in Mammalian Cell Lines," Methods in Molecular Biology, vol. 248 B.K.C. Lo, ed., Humana Press, Totowa, N.J. pp. 255-268.
Yong, C.S. (Sep. 14, 2006, e-pub. May 17, 2006). "Enhanced Anti-Tumor Activity and Alleviated Hepatotoxicity Of Clotrimazole-Loaded Suppository Using Poloxamer-Propylene Glycol Gel," International Journal Of Pharmaceutics 321(1-2):56-61.

METHODS OF PREPARING A POLOXAMER FOR USE IN CELL CULTURE MEDIUM

CROSS REFERENCE TO RELATED APPLICATIONS

This application is a divisional of U.S. patent application Ser. No. 15/273,155, filed Sep. 22, 2016, now U.S. Pat. No. 11,034,793, issued on Jun. 15, 2021, which is a continuation of International Application No. PCT/US2015/022592, filed internationally on Mar. 25, 2015, which claims the priority benefit of U.S. Provisional Application Ser. No. 61/970,281, filed Mar. 25, 2014, each of which is incorporated herein by reference in its entirety.

FIELD OF THE INVENTION

This invention relates to methods of preparing poloxamer (e.g., for use in a cell culture medium), cell culture media containing the poloxamer prepared as described herein, and methods of using the cell culture media described herein to culture cells and produce polypeptides.

BACKGROUND OF THE INVENTION

Cell culture manufacturing technology is widely used for the production of protein-based therapeutics, such as antibodies, for use in pharmaceutical formulations. Commercial production of protein-based products, such as an antibody product, requires optimization of cell culture parameters in order for the cell to produce a high amount of the protein product to meet manufacturing demands. When protein-based products are made on an industrial scale, factors such as the efficiency of protein production and the cost of raw materials (e.g., the components in the cell culture medium) are critically important.

Poloxamer is a component in cell culture medium that is widely used in industrial protein production. It is added to a cell culture medium to enhance the viability of the cultured cells. One of its many functions is to act as a surfactant, reducing the force of attachment between the cells and gas bubbles in the cell culture medium and protecting the cells from damage when the bubbles burst. It may also strengthen cell membranes, improve cell drainage from the foam layer of the culture, and alter bubble frequency and velocity.

Unfortunately, significant lot-to-lot variability in poloxamer performance has been observed. When used in a cell culture medium, poorly performing lots of poloxamer can cause reduced cell viability and cell growth rate. Reduced cell viability leads to reduced protein production. When culturing is performed on an industrial scale, this reduced production can result in serious financial losses.

Therefore, a need exists for a simple, inexpensive solution to reduce poloxamer variability and to improve poloxamer performance, particularly for poorly performing lots.

All publications, patents, and patent applications cited herein are hereby incorporated by reference in their entirety for all purposes.

SUMMARY OF THE INVENTION

The invention provided herein discloses, inter alia, methods of preparing a poloxamer (e.g., for use in a cell culture medium). Also provided are poloxamers prepared by the methods described herein. Further disclosed herein are cell culture media compositions containing a poloxamer prepared by the methods described herein. Further disclosed herein are methods of producing a polypeptide in a cell culture by culturing a cell that produces the polypeptide in a cell culture medium containing a poloxamer prepared by the methods described herein.

Accordingly, in one aspect, provided herein are methods of preparing a poloxamer for use in a cell culture medium, comprising the steps of: (a) heating a solid poloxamer to at least about 60° C. to form a liquid poloxamer; and (b) cooling the liquid poloxamer to a temperature below about 50° C. to form a solid heat-treated poloxamer, wherein the cooling is not conducted in a prilling or milling device, and wherein the poloxamer comprises a copolymer of ethylene oxide and propylene oxide. In some embodiments, cell viability in a cell culture medium comprising the heat-treated poloxamer is increased as compared to cell viability in a cell culture medium comprising the poloxamer before step (a). In some embodiments, the poloxamer in step (a) is heated to between about 60° C. and about 185° C. In some embodiments, the poloxamer in step (a) is heated to between about 157° C. and about 185° C. In some embodiments, the poloxamer is heated to between about 157° C. and about 185° C. for at least 1 minute. In some embodiments, the poloxamer is heated to between about 157° C. and about 185° C. for between 1 minute and about 250 minutes. In some embodiments, the poloxamer in step (a) is heated to between about 134° C. and about 157° C. In some embodiments, the poloxamer is heated to between about 134° C. and about 157° C. for at least 1 minute. In some embodiments, the poloxamer is heated to between about 134° C. and about 157° C. for between 1 minute and about 250 minutes. In some embodiments, the poloxamer in step (a) is heated to between about 120° C. and about 134° C. In some embodiments, the poloxamer is heated to between about 120° C. and about 134° C. for at least about 62 minutes. In some embodiments, the poloxamer is heated to between about 120° C. and about 134° C. for between about 62 minutes and about 250 minutes. In some embodiments, the poloxamer in step (a) is heated to between about 100° C. and about 120° C. In some embodiments, the poloxamer is heated to between about 100° C. and about 120° C. for at least about 98 minutes. In some embodiments, the poloxamer is heated to between about 100° C. and about 120° C. for between about 98 minutes and about 250 minutes. In some embodiments, the poloxamer in step (a) is heated to between about 80° C. and about 100° C. In some embodiments, the poloxamer is heated to between about 80° C. and about 100° C. for at least about 122 minutes. In some embodiments, the poloxamer is heated to between about 80° C. and about 100° C. for between about 122 minutes and about 250 minutes. In some embodiments, the poloxamer in step (a) is heated to between about 60° C. and about 80° C. In some embodiments, the poloxamer is heated to between about 60° C. and about 80° C. for at least about 143 minutes. In some embodiments, the poloxamer is heated to between about 60° C. and about 80° C. for between about 143 minutes and about 250 minutes. In some embodiments, cell viability in a cell culture medium comprising the heat-treated poloxamer is increased by at least 10% as compared to cell viability in a cell culture medium comprising the poloxamer before step (a). In some embodiments, the cell viability is increased by at least about 20%. In some embodiments, the cell viability is increased by at least about 30%. In some embodiments, the cell viability in a cell culture medium comprising the poloxamer before step (a) is below about 80% after about 3 hours of cell culturing. In some embodiments, the liquid poloxamer in step (b) is cooled at ambient temperature, about 2° C. to about 8° C., or below 0° C. In some embodiments, the poloxamer is heated under a vacuum. In some embodiments, the liquid poloxamer is cooled for at least about 20 minutes. In some embodiments, the heated-treated poloxamer produced in step (b) is added into a cell culture medium. In some embodiments, steps (a) and (b) are repeated at least once before adding the heated-treated poloxamer into the cell culture medium. In some embodiments, the poloxamer has been treated by a prilling process before step (a). In some embodiments, the poloxamer has a formula of $HO(C_2H_4O)_n(C_3H_6O)_m(C_2H_4O)_nH$, wherein n is from about 60 to about 150 and m is from about 25 to about 60. In some embodiments, the poloxamer has a melting temperature of about 55° C. In some embodiments, the poloxamer has an average molecular weight of from about 6,000 to about 18,000 Daltons. In some embodiments, the poloxamer comprises a copolymer having a formula of $HO(C_2H_4O)_n(C_3H_6O)_m(C_2H_4O)_nH$ with n having a value of about 80, with m having a value of about 27, and the poloxamer has an average molecular weight of from about 7680 to about 9510 g/mol. In some embodiments, the poloxamer is poloxamer 188. In some embodiments, the cell is a mammalian cell. In some embodiments, the cell is a Chinese Hamster Ovary (CHO) cell. In some embodiments, the cell is an insect cell. In some embodiments, the cell produces a polypeptide.

In another aspect, provided herein is a poloxamer prepared by any of the methods described above and herein.

In a further aspect, provided herein is a cell culture medium comprising the poloxamer prepared by any of the methods described above and herein. In some embodiments, the cell medium comprises the heat-treated poloxamer at about 0.1 g/L to about 10 g/L. In some embodiments, the cell medium comprises the heat-treated poloxamer at about 0.1 g/L to about 3 g/L. In some embodiments, the cell medium comprises the heat-treated poloxamer at about 3 g/L to about 10 g/L.

In a still further aspect, provided herein are methods of producing a polypeptide in a cell culture, comprising the step of culturing a cell that produces the polypeptide in a cell culture medium under conditions suitable for production of the polypeptide, wherein the cell culture medium comprises the poloxamer produced by any of the methods described above and herein. In some embodiments, the cell is a mammalian cell. In some embodiments, the cell is a Chinese Hamster Ovary (CHO) cell. In some embodiments, the cell is an insect cell. In some embodiments, the cell medium comprises the heat-treated poloxamer at about 0.1 g/L to about 10 g/L. In some embodiments, the cell medium comprises the heat-treated poloxamer at about 0.1 g/L to about 3 g/L. In some embodiments, the cell medium comprises the heat-treated poloxamer at about 3 g/L to about 10 g/L. In some embodiments, the polypeptide is an antibody or antigen-binding fragment thereof.

Accordingly, in one aspect, provided herein are methods of preparing a poloxamer (e.g., for use in a cell culture medium), comprising the steps of (a) heating a purified poloxamer to about 80° C. or above (e.g., about 80° C. to about 100° C.) to form a liquid poloxamer, and (b) cooling the liquid poloxamer to a temperature at about 50° C. or below to form a solid heat-treated poloxamer, wherein the cooling is not conducted in a prilling or milling device. In some embodiments, the poloxamer comprises a copolymer of ethylene oxide and propylene oxide. In some embodiments, the poloxamer comprises a copolymer of ethylene oxide and propylene oxide having a formula of $HO(C_2H_4O)_n(C_3H_6O)_m(C_2H_4O)_nH$, wherein n is from about 60 to about 150 and m is from about 25 to about 60.

In some embodiments, cell viability in a cell culture medium comprising the heat-treated poloxamer is increased as compared to cell viability in a cell culture medium comprising the poloxamer before step (a). In some embodiments, the poloxamer is a purified poloxamer. In some embodiments, a purified poloxamer is a poloxamer composition that does not contain another therapeutic or pharmaceutical compound. In some embodiments, the poloxamer in step (a) does not contain another therapeutic or pharmaceutical compound. In some embodiments, the poloxamer in step (a) is heated to about 85° C. to about 91° C. In some embodiments herein, the poloxamer is heated from about 10 to about 15 minutes. In some embodiments herein, the liquid poloxamer in step (b) is cooled at ambient temperature, about 2° C. to about 8° C., or below 0° C. In some embodiments herein, the liquid poloxamer is cooled for at least about 20 minutes. In some embodiments herein, the heated-treated poloxamer produced in step (b) is added into a cell culture medium. In some embodiments herein, steps (a) and (b) are repeated at least once before adding the heated-treated poloxamer into the cell culture medium. In some embodiments herein, the cell viability is increased by at least about 10%. In some embodiments herein, the cell viability is increased by at least about 30%. In some embodiments herein, the cell viability in a cell culture medium comprising the poloxamer before step (a) is below about 80%. In some embodiments herein, the poloxamer has been treated by a prilling process before step (a). In some embodiments herein, the poloxamer has a melting temperature in the range of about 45° C. to about 60° C. In some embodiments herein, the poloxamer has an average molecular weight of from about 6,000 to about 18,000 Daltons. In some embodiments herein, the poloxamer is poloxamer 188. In some embodiments, the poloxamer comprises a copolymer having a formula of $HO(C_2H_4O)_n(C_3H_6O)_m(C_2H_4O)_nH$ with n having a value of about 80, with m having a value of about 27, and the poloxamer has an average molecular weight of from about 7680 to about 9510 g/mol. In some embodiments herein, the poloxamer is poloxamer 237. In some embodiments, the poloxamer comprises a copolymer having a formula of $HO(C_2H_4O)_n(C_3H_6O)_m(C_2H_4O)_nH$ with n having a value of about 64 and with m having a value of about 37. In some embodiments herein, the poloxamer is poloxamer 338. In some embodiments, the poloxamer comprises a copolymer having a formula of $HO(C_2H_4O)_n(C_3H_6O)_m(C_2H_4O)_nH$ with n having a value of about 141 and with m having a value of about 44. In some embodiments herein, the poloxamer is poloxamer 407. In some embodiments, the poloxamer comprises a copolymer having a formula of $HO(C_2H_4O)_n(C_3H_6O)_m(C_2H_4O)_nH$ with n having a value of about 101 and with m having a value of about 56. In some embodiments herein, the cell may be a mammalian cell. In some embodiments, the cell may be a Chinese Hamster Ovary (CHO) cell. In some embodiments herein, the cell may be an insect cell. In some embodiments herein, the cell produces a polypeptide. In some embodiments, the polypeptide is an antibody or antigen-binding fragment thereof. In another aspect, provided herein is a poloxamer produced by any of the methods described above and herein.

In another aspect, provided herein are cell culture media comprising the poloxamer produced by any of the methods described above and herein. In some embodiments, the cell medium comprises the heat-treated poloxamer at about 0.1 g/L to about 10 g/L. In some embodiments, the cell medium comprises the heat-treated poloxamer at about 0.1 g/L to about 3 g/L. In some embodiments, the cell medium comprises the heat-treated poloxamer at about 3 g/L to about 10 g/L.

In another aspect, provided herein are methods of producing a polypeptide in a cell culture, comprising the step of culturing a cell that produces the polypeptide in a cell culture medium under conditions suitable for production of the polypeptide, wherein the cell culture medium comprises the poloxamer produced by any of the methods described above and herein. In some embodiments, the cell is a mammalian cell. In some embodiments, the cell is a Chinese Hamster Ovary (CHO) cell. In some embodiments, the cell is an insect cell. In some embodiments, the cell medium comprises the heat-treated poloxamer at about 0.1 g/L to about 10 g/L. In some embodiments, the cell medium comprises the heat-treated poloxamer at about 0.1 g/L to about 3 g/L. In some embodiments, the cell medium comprises the heat-treated poloxamer at about 3 g/L to about 10 g/L. In some embodiments, the polypeptide produced by the cell is an antibody or antigen-binding fragment thereof.

It is to be understood that one, some, or all of the properties of the various embodiments described herein may be combined to form other embodiments of the present invention. These and other aspects of the invention will become apparent to one of skill in the art.

DETAILED DESCRIPTION

Figure 1:
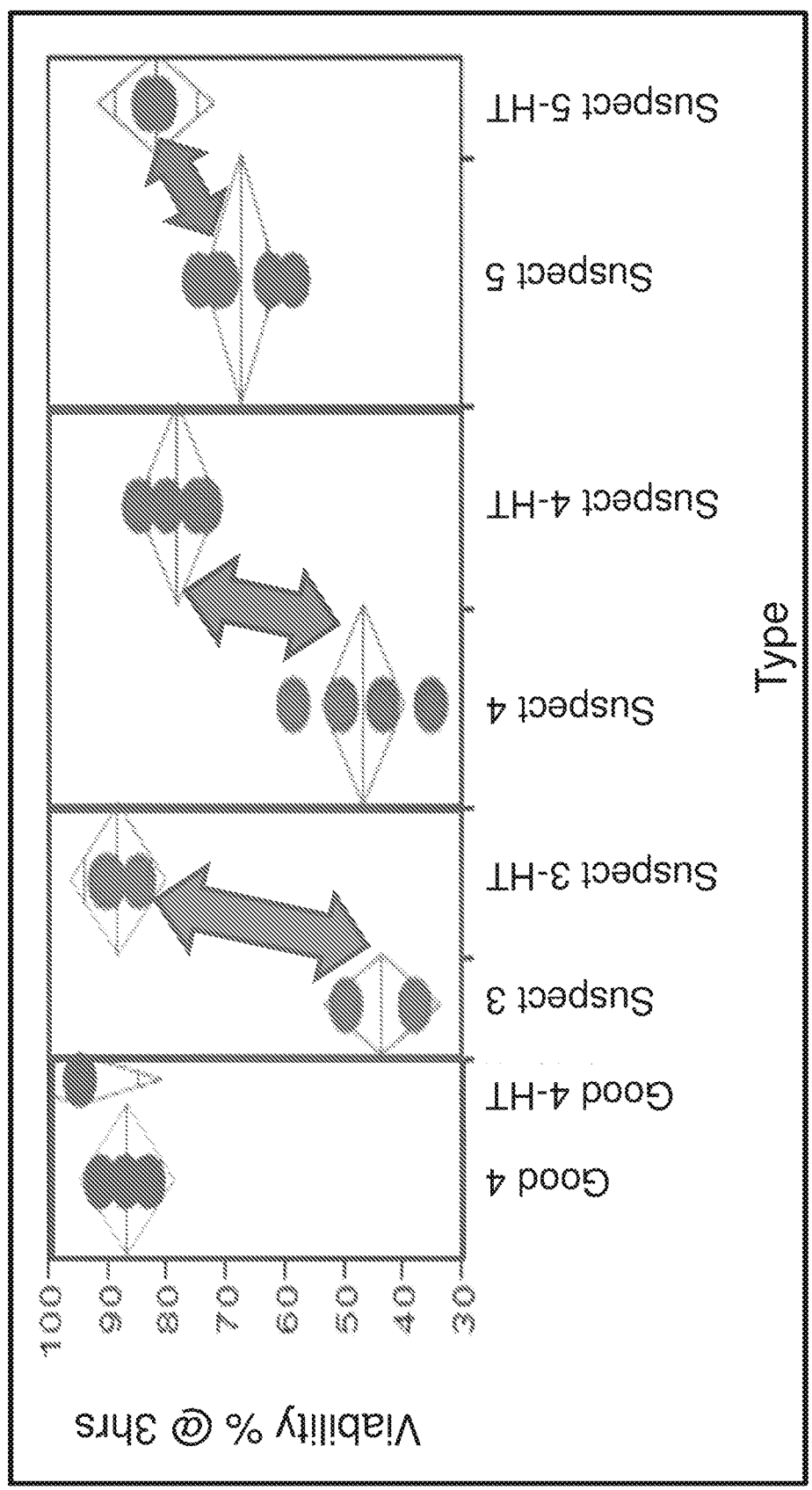
FIG. 1 shows that heat treatment of poloxamer improves its effect on cell viability in culture. The diamond plot indicates the mean (center line) and upper/lower 95% confidence intervals (points of diamonds), as well as the cell viability values (dots) for each experimental condition. Each experiment compares untreated and heat-treated (HT) poloxamer from a good or bad ("suspect") poloxamer lot, as indicated on the x-axis. Arrows indicate improvement in cell viability upon heat treatment of bad lots. Note that heat treatment also improved the cell viability of the good lot, from an average of approximately 85% to a value of approximately 95%.

The inventors of this application demonstrated that heat treatment of poloxamer improves the ability of the poloxamer to support viability in cell culture. The data in the application show that using a cell culture medium with the heat-treated poloxamer improves cell viability, compared to using a cell culture medium without the heat treatment. The inventors demonstrated that different lots of poloxamer, when added to cell culture medium, have dramatically different effects on cell viability, and that the heat treatment described herein improves the effect on cell viability for both good and bad lots of poloxamer.

In one aspect, provided herein are methods for preparing a poloxamer by heating a poloxamer and cooling the poloxamer, where the cooling is not conducted in a prilling or milling device. In some embodiments, the methods include preparing a poloxamer by heating a poloxamer to about 80° C. or above (e.g., to about 100° C.) to form a liquid poloxamer and cooling the liquid poloxamer to a temperature below about 50° C. to form a solid heat-treated poloxamer, where the cooling is not conducted in a prilling or milling device, and where the poloxamer contains a copolymer of ethylene oxide and propylene oxide. In some embodiments, the poloxamer contains a copolymer of ethylene oxide and propylene oxide having a formula of $HO(C_2H_4O)_n(C_3H_6O)_m(C_2H_4O)_nH$, where n is from about 60 to about 150 and m is from about 25 to about 60. In some embodiments, the poloxamer is a solid poloxamer before the heating and cooling process. In some embodiments, the poloxamer is a liquid poloxamer at room temperature before the heating and cooling process. In some embodiments, the poloxamer is a solid poloxamer dissolved in a liquid or aqueous solution before the heating and cooling process. For example, the methods provided herein may be used to prepare a poloxamer for use in a cell culture or cell culture medium.

In another aspect, provided herein are compositions for cell culture including a heat-treated poloxamer. In another aspect, provided herein are compositions for cell culture containing a heat-treated poloxamer in a cell culture medium.

In another aspect, provided herein are methods for producing a polypeptide in a cell culture by culturing a cell that produces the polypeptide in a cell culture medium containing a heat-treated poloxamer under conditions suitable for production of the polypeptide.

I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "poloxamer" refers to a block copolymer made of a chain of polyoxypropylene (the term "propylene oxide" may be used interchangeably herein) flanked by two chains of polyoxyethylene (the term "ethylene oxide" may be used interchangeably herein). Poloxamers may be sold under trade names including PLURONIC® (BASF), KOLLIPHOR® (BASF), LUTROL® (BASF), and SYNPERONIC® (Croda International). Unless a particular poloxamer species is specified, references to "poloxamer" may generically refer to multiple poloxamer species.

In some embodiments, the poloxamer is a purified poloxamer. The term "purified poloxamer" refers to a poloxamer composition that is substantially free from other compounds. A purified poloxamer may include, for example, a commercially available poloxamer having a grade of technical or higher. Examples of grades of technical or higher may include technical grade, purified grade, N.F. grade (US National Formulary), U.S.P. grade (US Pharmacopeia), reagent grade, and A.C.S. grade (American Chemical Society). A purified poloxamer refers to one that is not mixed with another compound. For example, a purified poloxamer may refer to a poloxamer that is not mixed with a therapeutic or pharmaceutical compound, e.g., as part of a drug formulation. In some embodiments, a purified poloxamer is one that is substantially free from, or not mixed with, unreacted reactants, catalysts or other products generated through a poloxamer synthesis process or reaction.

The term "heat-treated poloxamer" refers to a poloxamer heat treated at least once by the methods provided herein.

The terms "medium" and "cell culture medium" refer to a nutrient source used for growing or maintaining cells. As is understood by a person of skill in the art, the nutrient source may contain components required by the cell for growth and/or survival or may contain components that aid in cell growth and/or survival. Vitamins, essential or nonessential amino acids, trace elements, and surfactants (e.g., poloxamers) are examples of medium components. Any media provided herein may also be supplemented with any one or more of insulin, plant hydrolysates and animal hydrolysates.

"Culturing" a cell refers to contacting a cell with a cell culture medium under conditions suitable to the viability and/or growth and/or proliferation of the cell.

"Batch culture" refers to a culture in which all components for cell culturing (including the cells and all culture nutrients and components) are supplied to the culturing vessel at the start of the culturing process.

The phrase "fed batch cell culture," as used herein refers to a batch culture wherein the cells and culture medium are supplied to the culturing vessel initially, and additional culture nutrients are fed, continuously or in discrete increments, to the culture during the culturing process, with or without periodic cell and/or product harvest before termination of culture.

"Perfusion culture" is a culture by which the cells are restrained in the culture by, e.g., filtration, encapsulation, anchoring to microcarriers, etc., and the culture medium is continuously or intermittently introduced and removed from the culturing vessel.

"Culturing vessel" refers to a container used for culturing a cell. The culturing vessel can be of any size so long as it is useful for the culturing of cells.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Examples of polypeptides encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

The term "titer" as used herein refers to the total amount of recombinantly expressed antibody produced by a cell culture divided by a given amount of medium volume. Titer is typically expressed in units of milligrams of antibody per milliliter of medium. Titer can be expressed or assessed in terms of a relative measurement, such as a percentage increase in titer as compared obtaining the protein product under different culture conditions.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. An antibody can be human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen binding region (the term "antigen-binding fragment" may be used interchangeably) thereof. Examples of antibody fragments include Fab, Fab', F(ab')$_2$, and Fv fragments; diabodies; linear antibodies; single-chain antibody molecules; and multispecific antibodies formed from antibody fragments.

II. Methods of Preparing a Poloxamer

Provided herein are methods of preparing a poloxamer, for example, for use in a cell culture medium.

Heating

In some aspects, the methods of preparing a poloxamer for use in a cell culture medium provided herein include heating a poloxamer (e.g., a purified poloxamer) to form a liquid poloxamer. For example, a purified poloxamer in the solid phase may be heated to melt, thereby forming a liquid poloxamer. The temperature to which the poloxamer is heated may be adjusted based upon the melting temperature of the particular poloxamer species used. In some embodiments, the purified poloxamer has a melting temperature in the range of about 45° C. to about 60° C. In some embodiments, the purified poloxamer has a melting temperature in the range of about 50° C. to about 55° C.

In some embodiments, the methods of preparing a poloxamer for use in a cell culture medium provided herein include heating a solid poloxamer to at least about 60° C. to form a liquid poloxamer and cooling the liquid poloxamer to a temperature below about 50° C. to form a solid heat-treated poloxamer, where the cooling is not conducted in a prilling or milling device, and the poloxamer comprises a copolymer of ethylene oxide and propylene oxide. In some embodiments, the poloxamer is a purified poloxamer. In some embodiments, a purified poloxamer is a poloxamer composition that does not contain another therapeutic or pharmaceutical compound.

In some embodiments, the poloxamer (e.g., a purified poloxamer) is heated to at least about any of the following temperatures (in ° C.): 60, 65, 70, 75, 80, 85, 90, 95, 100, 105, 110, 115, 120, 125, 130, 135, 140, 145, 150, 155, 160, 165, 170, 175, 180, or 185. In some embodiments, the poloxamer (e.g., a purified poloxamer) is heated for at least 1 minute. In some embodiments, the poloxamer is heated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, at least about 65 minutes, at least about 70 minutes, at least about 75 minutes, at least about 80 minutes, at least about 85 minutes, at least about 90 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes.

In some embodiments, the poloxamer (e.g., a purified poloxamer) is heated to between about 60° C. and about 185° C. It is to be noted that any of the temperature ranges described herein are meant to be inclusive, unless explicitly stated otherwise. For example, a range of temperatures between about 60° C. and about 185° C. includes about 60° C. and about 185° C. as being within said range. In some embodiments, the poloxamer is heated to a temperature less than about any of the following temperatures (in ° C.): 185, 180, 175, 170, 165, 160, 155, 150, 145, 140, 135, 130, 125, 120, 115, 110, 105, 100, 95, 90, 85, 80, 75, 70, or 65. In some embodiments, the poloxamer is heated to a temperature greater than about any of the following temperatures (in ° C.): 60, 65, 70, 75, 80, 85, 90, 95, 100, 105, 110, 115, 120, 125, 130, 135, 140, 145, 150, 155, 160, 165, 170, 175, or 180. That is, the poloxamer may be heated to a temperature in the range of temperatures having an upper limit of 185, 180, 175, 170, 165, 160, 155, 150, 145, 140, 135, 130, 125, 120, 115, 110, 105, 100, 95, 90, 85, 80, 75, 70, or 65 and an independently selected lower limit of 60, 65, 70, 75, 80, 85, 90, 95, 100, 105, 110, 115, 120, 125, 130, 135, 140, 145, 150, 155, 160, 165, 170, 175, or 180, wherein the lower limit is less than the upper limit. In some embodiments, the poloxamer (e.g., a purified poloxamer) is heated to between about 60° C. and about 185° C. for at least 1 minute. In some embodiments, the poloxamer is heated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, at least about 65 minutes, at least about 70 minutes, at least about 75 minutes, at least about 80 minutes, at least about 85 minutes, at least about 90 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 60° C. and about 185° C. for between about 1 minute and about 250 minutes. It is to be noted that any of the time ranges described herein are meant to be inclusive, unless explicitly stated otherwise. For example, a range of times between about 1 minute and about 250 minutes includes about 1 minute and about 250 minutes as being within said range. In some embodiments, the poloxamer is heated for less than about any of the following times (in minutes): 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 25, 20, 15, 10, 9, 8, 7, 6, 5, 4, 3, or 2. In some embodiments, the poloxamer is heated for greater than about any of the following times (in minutes): 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, or 240. That is, the poloxamer may be heated for a time in the range of times having an upper limit of 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 25, 20, 15, 10, 9, 8, 7, 6, 5, 4, 3, or 2 and an independently selected lower limit of 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, or 2400, wherein the lower limit is less than the upper limit.

In some embodiments, the poloxamer (e.g., a purified poloxamer) is heated to between about 157° C. and about 185° C. In some embodiments, the poloxamer is heated to a temperature less than about any of the following temperatures (in ° C.): 185, 180, 175, 170, 165, or 160. In some embodiments, the poloxamer is heated to a temperature greater than about any of the following temperatures (in ° C.): 157, 160, 165, 170, 175, or 180. That is, the poloxamer may be heated to a temperature in the range of temperatures having an upper limit of 185, 180, 175, 170, 165, or 160 and an independently selected lower limit of 157, 160, 165, 170, 175, or 180, wherein the lower limit is less than the upper limit. In some embodiments, the poloxamer is heated to between about 157° C. and about 185° C. for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, at least about 65 minutes, at least about 70 minutes, at least about 75 minutes, at least about 80 minutes, at least about 85 minutes, at least about 90 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 157° C. and about 185° C. for less than or equal to 250 minutes.

In some embodiments, the poloxamer (e.g., a purified poloxamer) is heated to between about 134° C. and about 157° C. In some embodiments, the poloxamer is heated to a temperature less than about any of the following temperatures (in ° C.): 157, 155, 150, 145, 140, or 135. In some embodiments, the poloxamer is heated to a temperature greater than about any of the following temperatures (in ° C.): 134, 135, 140, 145, 150, or 155. That is, the poloxamer may be heated to a temperature in the range of temperatures having an upper limit of 157, 155, 150, 145, 140, or 135 and an independently selected lower limit of 134, 135, 140, 145, 150, or 155, wherein the lower limit is less than the upper limit. In some embodiments, the poloxamer is heated to between about 134° C. and about 157° C. for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, at least about 65 minutes, at least about 70 minutes, at least about 75 minutes, at least about 80 minutes, at least about 85 minutes, at least about 90 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 134° C. and about 157° C. for less than or equal to 250 minutes.

In some embodiments, the poloxamer (e.g., a purified poloxamer) is heated to between about 120° C. and about 134° C. In some embodiments, the poloxamer is heated to a temperature less than about any of the following temperatures (in ° C.): 134, 130, or 125. In some embodiments, the poloxamer is heated to a temperature greater than about any of the following temperatures (in ° C.): 120, 125, or 130. That is, the poloxamer may be heated to a temperature in the range of temperatures having an upper limit of 134, 130, or 125 and an independently selected lower limit of 120, 125, or 130, wherein the lower limit is less than the upper limit. In some embodiments, the poloxamer is heated to between about 120° C. and about 134° C. for at least about 20 minutes, at least about 30 minutes, at least about 40 minutes, at least about 50 minutes, or at least about 60 minutes. In some embodiments, the poloxamer is heated to between about 120° C. and about 134° C. for at least about 62 minutes, at least about 65 minutes, at least about 70 minutes, at least about 75 minutes, at least about 80 minutes, at least about 85 minutes, at least about 90 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 120° C. and about 134° C. for less than or equal to 250 minutes.

In some embodiments, the poloxamer (e.g., a purified poloxamer) is heated to between about 100° C. and about 120° C. In some embodiments, the poloxamer is heated to a temperature less than about any of the following temperatures (in ° C.): 120, 115, 110, or 105. In some embodiments, the poloxamer is heated to a temperature greater than about any of the following temperatures (in ° C.): 100, 105, 110, or 115. That is, the poloxamer may be heated to a temperature in the range of temperatures having an upper limit of 120, 115, 110, or 105 and an independently selected lower limit of 100, 105, 110, or 115, wherein the lower limit is less than the upper limit. In some embodiments, the poloxamer is heated to between about 100° C. and about 120° C. for at least about 20 minutes, at least about 30 minutes, at least about 40 minutes, at least about 50 minutes, or at least about 60 minutes, at least about 70 minutes, at least about 80 minutes, or at least about 90 minutes. In some embodiments, the poloxamer is heated to between about 100° C. and about 120° C. for at least about 98 minutes, at least about 100 minutes, at least about 110 minutes, at least about 120 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 100° C. and about 120° C. for less than or equal to 250 minutes.

In some embodiments, the poloxamer (e.g., a purified poloxamer) is heated to between about 80° C. and about 100° C. In some embodiments, the poloxamer is heated to a temperature less than about any of the following temperatures (in ° C.): 100, 95, 90, or 85. In some embodiments, the poloxamer is heated to a temperature greater than about any of the following temperatures (in ° C.): 80, 85, 90, or 95. That is, the poloxamer may be heated to a temperature in the range of temperatures having an upper limit of 100, 95, 90, or 85 and an independently selected lower limit of 80, 85, 90, or 95, wherein the lower limit is less than the upper limit. In some embodiments, the poloxamer is heated to between about 80° C. and about 100° C. for at least about 20 minutes, at least about 30 minutes, at least about 40 minutes, at least about 50 minutes, or at least about 60 minutes, at least about 70 minutes, at least about 80 minutes, or at least about 90 minutes, at least about 100 minutes, at least about 110 minutes, or at least about 120 minutes. In some embodiments, the poloxamer is heated to between about 80° C. and about 100° C. for at least about 122 minutes, at least about 130 minutes, at least about 140 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 80° C. and about 100° C. for less than or equal to 250 minutes.

In some embodiments, the poloxamer (e.g., a purified poloxamer) is heated to between about 60° C. and about 80° C. In some embodiments, the poloxamer is heated to a temperature less than about any of the following temperatures (in ° C.): 80, 75, 70, or 65. In some embodiments, the poloxamer is heated to a temperature greater than about any of the following temperatures (in ° C.): 60, 65, 70, or 75. That is, the poloxamer may be heated to a temperature in the range of temperatures having an upper limit of 80, 75, 70, or 65 and an independently selected lower limit of 60, 65, 70, or 75, wherein the lower limit is less than the upper limit. In some embodiments, the poloxamer is heated to between about 60° C. and about 80° C. for at least about 20 minutes, at least about 30 minutes, at least about 40 minutes, at least about 50 minutes, or at least about 60 minutes, at least about 70 minutes, at least about 80 minutes, or at least about 90 minutes, at least about 100 minutes, at least about 110 minutes, at least about 120 minutes, at least 130 minutes, or at least 140 minutes. In some embodiments, the poloxamer is heated to between about 60° C. and about 80° C. for at least about 143 minutes, at least about 150 minutes, at least about 160 minutes, at least about 170 minutes, at least about 180 minutes, at least about 190 minutes, at least about 200 minutes, at least about 210 minutes, at least about 220 minutes, at least about 230 minutes, or at least about 240 minutes. In some embodiments, the poloxamer is heated to between about 60° C. and about 80° C. for less than or equal to 250 minutes.

In some embodiments, the poloxamer is heated under a vacuum. For example, the poloxamer may be heated in a vacuum oven under an applied vacuum. As described below, it was unexpectedly found that heating poloxamer at the temperatures described herein under an applied vacuum results in improved poloxamer performance (see, e.g., Example 7). Stated another way, applying a vacuum to the poloxamer during heating does not negate the beneficial effects of heating on subsequent poloxamer performance, e.g., in cell culture.

In other embodiments, heating a poloxamer to a target temperature for a period of time may refer to the time during which the poloxamer is at the particular temperature. That is to say, time=0 may indicate the time at which the poloxamer reached the target temperature. For example, heating a poloxamer to 140° C. for 5 minutes may indicate that the poloxamer was heated for 5 minutes after reaching a temperature of 140° C. For example, heating a poloxamer (e.g., a purified poloxamer) to between about 60° C. and about 185° C. for at least 1 minute indicates that the poloxamer has achieved the target temperature (e.g., between about 60° C. and about 185° C.) for at least 1 minute.

In some embodiments, the temperature of the purified poloxamer during heating process does not exceed about 120° C. In some embodiments, the purified poloxamer may be dissolved in a liquid or aqueous solution before the heating process. In some embodiments, the purified poloxamer dissolved in a liquid or aqueous solution may be heated to a higher temperature than would be used for a solid poloxamer. In some embodiments, the purified poloxamer is a solid poloxamer before the heating process. In some embodiments, the purified poloxamer is a liquid poloxamer at room temperature before the heating process.

In some embodiments, the purified poloxamer is heated to a temperature of about 80° C. to about 100° C. In some embodiments, the purified poloxamer is heated to a temperature of about 85° C. to about 91° C. In some embodiments, the purified poloxamer is heated to a temperature less than about any of the following temperatures (in ° C.): 100, 99, 98, 97, 96, 95, 94, 93, 92, 91, 90, 89, 88, 87, 86, 85, 84, 83, 82, or 81. In some embodiments, the purified poloxamer is heated to a temperature greater than about any of the following temperatures (in ° C.): 80, 81, 82, 83, 84, 85, 86, 87, 88, 89, 90, 91, 92, 93, 94, 95, 96, 97, 98, or 99. That is, the purified poloxamer may be heated to a temperature in the range of temperatures having an upper limit of 100, 99, 98, 97, 96, 95, 94, 93, 92, 91, 90, 89, 88, 87, 86, 85, 84, 83, 82, or 81 and an independently selected lower limit of 80, 81, 82, 83, 84, 85, 86, 87, 88, 89, 90, 91, 92, 93, 94, 95, 96, 97, 98, or 99, wherein the lower limit is less than the upper limit. In some embodiments, the purified poloxamer is heated to a temperature of less than about 120° C. In some embodiments, the purified poloxamer is heated to a temperature of less than about any of 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., and 119° C.

The purified poloxamer may be heated for any desired period of time. In some embodiments, the purified poloxamer is heated for about 10 to about 15 minutes. The heating time may refer to the total time during which heat is applied to the poloxamer, so the heating time is not limited to the time during which the poloxamer has achieved the desired temperature. In some embodiments, the purified poloxamer is heated for a total amount of time between about 10 and about 15 minutes, and the heating is stopped when the poloxamer achieves a desired maximal temperature, e.g., about 80° C. to about 100° C.

Any suitable heating apparatus known in the art may be used to heat the purified poloxamer. As a non-limiting example, the solid poloxamer may be heated in a glass container (e.g., a PYREX® beaker, flask, or other open vessel) that is heated on a standard laboratory heating plate (e.g., a stirring hotplate sold by Corning®, Costar®, or Thermo Scientific™). Alternatively, the poloxamer may be heated in a vacuum oven.

Any suitable temperature measurement tool known in the art may be used to measure the temperature of the poloxamer during/after heat treatment, provided that the temperature measurement tool is used in such a way that an accurate measurement of poloxamer temperature may be made (e.g., according to manufacturer's instructions for use). Non-limiting examples of suitable temperature measurement tools include without limitation thermometers (e.g., liquid-in-glass thermometers), thermocouples (e.g., as described below), resistance temperature detectors (RTDs), and/or thermistors. In some embodiments, the temperature measurement tool may be intrinsic to the equipment used for heating.

Cooling

In some aspects, the methods of preparing a poloxamer for use in a cell culture medium described herein include cooling a heated, purified poloxamer to form a solid heat-treated poloxamer. In some embodiments, the liquid poloxamer is cooled to a temperature below about 50° C. The temperature to which the liquid poloxamer is cooled may be any temperature below its freezing temperature, which may vary depending upon the particular poloxamer used. For example, poloxamer 188 has a freezing temperature of about 52° C., so this poloxamer may be cooled to any temperature below about 52° C. to form a solid heat-treated poloxamer.

The heated liquid poloxamer may be cooled at any temperature sufficient for the poloxamer to freeze. In some embodiments, the heated liquid poloxamer is cooled at ambient temperature. In some embodiments, the heated liquid poloxamer is cooled at about 2° C. to about 8° C. In some embodiments, the heated liquid poloxamer is cooled at below about 0° C., e.g., at about −20° C. or at about −70° C.

The heated liquid poloxamer may be cooled for any desired duration of time sufficient for the heated liquid poloxamer to freeze at that cooling temperature. In some embodiments, the liquid poloxamer is cooled for about 20 minutes. The cooling time may depend on the temperature to which the poloxamer was heated and/or the cooling temperature. Cooling temperatures and times may be empirically determined by observing how long a liquid poloxamer (heated to a given temperature for a given amount of time) takes to freeze at a particular cooling temperature.

Any suitable cooling apparatus known in the art, except for a prilling or milling device, may be used to cool the heated liquid poloxamer. For example, the heated liquid poloxamer may be placed in a refrigerator, freezer, or cold room maintained at a sufficient cooling temperature as described above. Alternatively, no particular cooling apparatus may be used, but instead the heated liquid poloxamer may be cooled in the heating apparatus after the apparatus has been turned off or programmed to stop heating. In this case, the heated liquid poloxamer is allowed to cool at ambient temperature. For example, if the poloxamer is heated on a hotplate, the heated liquid poloxamer may be cooled simply by leaving it on the hotplate after the hotplate's heating function is turned off. Alternatively, the poloxamer may be cooled in a vacuum oven. In some embodiments, cooling the heated liquid poloxamer does not include using liquid nitrogen. In some embodiments, cooling the heated liquid poloxamer does not include spraying or atomizing the heated liquid poloxamer through a gas maintained at a specific temperature. In some embodiments, cooling the heated liquid poloxamer does not include shaping the poloxamer into particles or micro-particles of a specific or uniform size and/or shape.

Prilling/Milling

In some embodiments, the cooling is not conducted in a prilling or milling device. Poloxamer has been prepared in the art by prilling or milling to achieve a specific, uniform poloxamer particle size and/or shape (for an example describing poloxamer prilling and milling, see European Patent EP1661558 B1 or U.S. Pat. No. 7,887,844). Poloxamer prilling involves passing liquid poloxamer through an atomizer to create liquid poloxamer particles and cooling these particles in a cooling medium, e.g., a gas maintained at a specific temperature or liquid nitrogen. The temperature of the cooling medium is thought to determine the freezing rate of the poloxamer, which influences the final size and shape of the poloxamer particles. An example of a prilling device may include, without limitation, a prilling tower. In a prilling tower, an atomized poloxamer is released from the top of the tower, and it freezes into particles while falling through a gas or liquid cooling medium (e.g., ambient air, air maintained at a specific temperature, or liquid nitrogen).

Poloxamer milling (or micro-milling) involves grinding a solid poloxamer, or forcing a solid poloxamer by high pressure through a nozzle, until poloxamer particles of a certain size are produced. Because milling may generate heat and poloxamers have a relatively low melting temperature, the poloxamer is often cooled during the milling process to maintain a solid phase, e.g., by chilling with cooled air or liquid nitrogen. The poloxamer may also be cooled prior to milling and milled for a period of time insufficient for the poloxamer to melt. Examples of milling devices may include without limitation air-jet mills, ball-mills, and freezer mills (e.g., SPEX SamplePrep® Freezer/Mill).

Prilling and milling are useful for processes that require rigorous standards for poloxamer particle size and shape, for example as part of drug formulations. Poloxamer is known in the art as a component in drug formulations that aids solubility and affects drug release. In these formulations, poloxamer particles must maintain standard characteristics in order to impart the desired pharmacokinetic properties of the drug formulation and adhere to rigorous drug safety and reproducibility standards. It is noted that the methods described herein do not require such rigorous or precise standards for poloxamer, so these prilling or milling methods are not used.

In some embodiments, the poloxamer has been treated by a prilling process before it is heated as described herein. Many commercially available poloxamers for use in cell culture (e.g., Pluronic® F68 NF Frill Poloxamer 188 as sold by BASF®) have undergone a prilling or micro-prilling process during manufacture. The heating and cooling steps included in the methods described herein do not involve prilling. Rather, they may be applied to poloxamer that has already been prilled or micro-prilled. It is a discovery of the present disclosure that the performance of commercially available poloxamers (e.g., prilled or micro-prilled poloxamer) in cell culture may be improved by heating and cooling as described herein.

In some aspects, the methods of preparing a poloxamer for use in a cell culture medium described herein include adding a heat-treated poloxamer into a cell culture medium. After heating and cooling, the solid heat-treated poloxamer may be dissolved in a cell culture medium by any method known in the art. For example, if the poloxamer is heated and cooled in an open glass vessel, the resulting solid heat-treated poloxamer may simply be scraped or flaked off in an appropriate amount (by weight) to add to the cell culture medium. The heat-treated poloxamer may be added to a cell culture medium immediately, or it may be stored and added to a cell culture medium at a later time (e.g., more than about a day, more than about a month, or more than about a year after heat treatment).

In some embodiments, the heating and cooling steps as described above are each performed once before adding the heat-treated poloxamer into the cell culture medium. In some embodiments, the heating and cooling steps as described above are repeated at least once before adding the heat-treated poloxamer into the cell culture medium.

III. Poloxamers and Poloxamer Properties

Provided herein are methods for preparing a poloxamer. In some embodiments, the poloxamer produced by the methods is for use in a cell culture medium.

The term "poloxamer" may encompass many distinct compounds because different lengths for the polyoxypropylene and polyoxyethylene chains may be used in combination. The particular combination of polyoxypropylene and polyoxyethylene chains present in a poloxamer may give rise to particular chemical and/or biophysical properties. In some embodiments, the poloxamer has the chemical formula of $HO(C_2H_4O)_n(C_3H_6O)_m(C_2H_4O)_nH$. In some embodiments, n (i.e., the polyoxyethylene chain length) has a value from about 60 to about 150. In some embodiments, m (i.e., the polyoxypropylene chain length) has a value from about 25 to about 60.

Poloxamers are often described by a numbering system that designates their approximate molecular weight and percentage of polyoxyethylene content. These values may refer to an average value in a poloxamer composition, rather than an absolute value of each poloxamer molecule in the composition. Under this system, the first two digits are multiplied by 100 to give the approximate molecular weight of the polyoxypropylene block, and the third digit is multiplied by 10 to give the percentage by weight of the polyoxyethylene block. For example, poloxamer 188 (CAS No. 9003-11-6) may refer to a poloxamer with n having a value of about 80 and with m having a value of about 27 as in the formula depicted above. Poloxamer 237 may refer to a poloxamer with n having a value of about 64 and with m having a value of about 37. Poloxamer 338 may refer to a poloxamer with n having a value of about 141 and with m having a value of about 44. Poloxamer 407 may refer to a poloxamer with n having a value of about 101 and with m having a value of about 56. In some embodiments, the poloxamer has an average molecular weight of from about 6,000 to about 18,000 daltons. In some embodiments, poloxamer 188 may refer to a poloxamer with n having a value of about 80, with m having a value of about 27 as in the formula depicted above, and with the poloxamer having an average molecular weight of from about 7680 to about 9510 g/mol. In some embodiments, poloxamer 188 may refer to a poloxamer with n having a value of about 80, with m having a value of about 27 as in the formula depicted above, and with the poloxamer having an average molecular weight of from about 7000 to about 10000 g/mol.

Poloxamers sold under trade names, e.g., PLURONIC®, may be named under a different system. A letter may be used to indicate the physical state (e.g., F for solid, P for paste, or L for liquid). A 2 or 3 digit number may be used to indicate the chemical properties. The first one or two digits are multiplied by 300 to give the approximate molecular weight of the polyoxypropylene block, and the third digit is multiplied by 10 to give the percentage by weight of the polyoxyethylene block. For example, PLURONIC® F68 may refer to a solid poloxamer with n having a value of about 80 and with m having a value of about 27 as in the formula depicted above. PLURONIC® F87 may refer to a solid poloxamer with n having a value of about 64 and with m having a value of about 37. PLURONIC® F108 may refer to a solid poloxamer with n having a value of about 141 and with m having a value of about 44. PLURONIC® F127 may refer to a solid poloxamer with n having a value of about 101 and with m having a value of about 56.

Since poloxamers have both hydrophobic (polyoxypropylene) and hydrophilic (polyoxyethylene) moieties of various lengths, different poloxamers may possess different hydrophilic-lipophilic balances (HLBs). The HLB of a compound is determined by calculating the relative proportion of the compound that is hydrophilic or lipophilic, and the HLB value is used to predict the surfactant properties of a compound. For example, a compound with an HLB less than 10 is predicted to be water insoluble, and a compound with an HLB greater than 10 is predicted to be water soluble. In preferred embodiments, the poloxamer for use in cell culture has an HLB of 24 or above. The HLB of a poloxamer may be calculated according to methods well known in the art, including those described in Griffin, W. C. (1954) *J. Soc. Cosmet. Chemists* 5(4):249-56 and Davies, J. T. (1957) *Gas/Liquid and Liquid/Liquid Interfaces: Proc. of $2^{nd}$ Intl. Congress Surface Activity*, Butterworths (London): 426-38.

In some embodiments, physical and/or chemical properties of a poloxamer may be measured. For example, physical and/or chemical properties of a poloxamer may be measured before and after heat-treatment as described herein to identify properties associated with a heat-treated poloxamer. As another example, physical and/or chemical properties of a good poloxamer lot and a bad poloxamer lot as described herein may be measured to identify properties associated with a good poloxamer lot.

Examples of assays to measure physical and/or chemical properties may include, without limitation, MALDI-MS, Gel Permeation Chromatography, Powder-XRD, Quasi-elastic light scattering, and solid state NMR. MALDI-MS (Matrix-associated laser desorption/ionization mass spectrometry) is known in the art as a technique for analyzing, quantifying, or identifying a compound, e.g., by its molecular mass and charge. As a non-limiting example, MALDI-MS may be used to identify a compound (e.g., an impurity) preferentially associated with or present in a poloxamer lot before heat treatment or a bad poloxamer lot, compared to a heat-treated poloxamer or a good poloxamer lot. Gel Permeation Chromatography is known in the art as a technique for separating compounds by size. As a non-limiting example, Gel Permeation Chromatography may be used to isolate a compound (e.g., an impurity) preferentially associated with or present in a poloxamer lot before heat treatment or a bad poloxamer lot, compared to a heat-treated poloxamer or a good poloxamer lot. Powder-XRD (Powder X-ray Diffraction) is known in the art as a technique for characterizing the structure a compound and may involve the steps of generating a powder sample of a compound (containing a plurality of randomly oriented crystallites) and using X-ray diffraction to analyze structural features of the crystallites. As a non-limiting example, Powder-XRD may be used to characterize a structural property of a heat-treated poloxamer or a good poloxamer lot, e.g., compared to a poloxamer before heat treatment or a bad poloxamer lot. Quasi-elastic light scattering (a.k.a. dynamic light scattering and photon correlation spectroscopy) is known in the art as a technique for determining a size distribution profile of particles in a solution or suspension. As a non-limiting example, Quasi-elastic light scattering may be used to identify a compound (e.g., an impurity) by its particle size that is preferentially associated with or present in a poloxamer lot before heat treatment or a bad poloxamer lot, compared to a heat-treated poloxamer or a good poloxamer lot.

Solid state NMR (nuclear magnetic resonance, or SSNMR) is known in the art as a technique for determining a variety of structural features of a compound. For example, solid state NMR may be used to characterize a molecular conformation, arrangement, chemical shift, or polymorphic nature of a compound. As a non-limiting example, solid state NMR may be used to characterize a structural property of a heat-treated poloxamer or a good poloxamer lot, compared to a poloxamer before heat treatment or a bad poloxamer lot. In some embodiments, a structural property determined by solid state NMR may include the ratio of crystalline to amorphous poloxamer in a poloxamer sample. As another non-limiting example, solid state NMR may be used to provide spectra that can resolve or profile one or more poloxamer polymorphs. In some embodiments, solid state NMR may be used to resolve one or more poloxamer polymorphs in a good poloxamer lot or a heat-treated poloxamer, as compared to the poloxamer polymorphs present in a bad poloxamer lot or a poloxamer before heat treatment. In some embodiments, a poloxamer spectrum generated by solid state NMR may be correlated with the performance of a poloxamer in a cell culture medium, e.g., by measuring the cell viability of a cell culture grown in a cell culture medium containing a good poloxamer lot or a heat-treated poloxamer, as compared to the cell viability of a cell culture grown in a cell culture medium containing a bad poloxamer lot or a poloxamer before heat treatment.

IV. Use of Poloxamers in Cell Culture and Production of Polypeptides

Heat-treated poloxamers provided herein may find use in methods (e.g., of culturing cells and producing polypeptides using a culture medium containing a heat-treated poloxamer of the present disclosure) and in compositions (e.g., a cell culture medium containing a heat-treated poloxamer of the present disclosure).

Use of Poloxamer in Cell Culture

Poloxamers can be used as additives to cell culture media known in the art. Without wishing to be bound to theory, it is thought that poloxamers have many functions in cell culture media that may protect cells from damage and enhance cell viability. For example, poloxamer may act as a shear protectant to cells. Poloxamer may reduce cell-bubble attachment and/or reduce shock when bubbles burst, thereby preventing cell damage. Poloxamer may also alter bubble velocity and frequency, improve cell drainage from the foam layer, and/or strengthen cell membranes. See, e.g., Meier, S. J., et al. (1999) *Biotechnol. Bioeng.* 62(4):468-78; Chisti, Y. (2000) *Trends Biotechnol.* 18(10):420-32; and Tharmalingam, T., et al. (2008) *Mol. Biotechnol.* 39(2): 167-77.

Heat-treated poloxamer as described herein may be added to a cell culture medium at any concentration typically used for poloxamer. In some embodiments, the cell culture medium includes the heat-treated poloxamer at about 0.1 g/L to about 10 g/L. In some embodiments, the cell culture medium includes the heat-treated poloxamer at about 0.1 g/L to about 3 g/L. In some embodiments, the cell culture medium includes the heat-treated poloxamer at about 3 g/L to about 10 g/L. In some embodiments, the cell culture medium includes the heat-treated poloxamer at about 0.1 g/L, at about 0.2 g/L, at about 0.3 g/L, at about 0.4 g/L, at about 0.5 g/L, at about 0.6 g/L, at about 0.7 g/L, at about 0.8 g/L, at about 0.9 g/L, at about 1 g/L, at about 2 g/L, at about 3 g/L, at about 4 g/L, at about 5 g/L, at about 6 g/L, at about 7 g/L, at about 8 g/L, at about 9 g/L, or at about 10 g/L. In some embodiments, a heat-treated poloxamer prepared as described herein may be used at a lower concentration in a cell culture medium to achieve a desired level of cell viability than a poloxamer before heat treatment. In some embodiments, a heat-treated poloxamer prepared as described herein may be used at a more consistent or standardized concentration in a cell culture medium to achieve a desired level of cell viability than a poloxamer before heat treatment.

Surfactants such as poloxamers have a limit in solution, termed the critical micelle concentration (CMC), beyond which additional surfactant molecules added begin to be incorporated into micelles, rather than dissolving into the solution. At concentrations higher than the CMC, the surface tension of the solution no longer decreases at the same rate proportional to the concentration of surfactant. In preferred embodiments, the heat-treated poloxamer is added to a cell culture medium at a concentration lower than its CMC. For example, the CMC of poloxamer 188 has been determined to be 100 mg/mL (Kabanov, A. V., et al. (1995) *Macromolecules* 28(7):2303-14). The CMC of a poloxamer may be determined by measuring the surface tension of a solution while the poloxamer is added. The concentration at which increasing the poloxamer concentration no longer results in increased surface tension is the CMC for that poloxamer. Surface tension may be measured, for example and without limitation, using a tensiometer (e.g., Sigma 700/701 tensiometer from Attension).

Cell Culture Media

Certain aspects of the present disclosure relate to culturing a cell in a cell culture medium. Any cell culture medium known in the art, suitable for the desired type of cell and/or polypeptide product, may be used. In some embodiments, the cell culture medium is a chemically defined medium. In other embodiments, the cell culture medium is a chemically undefined medium. In some embodiments, a heat-treated poloxamer as described herein is added to a basal cell culture medium. In some embodiments, a heat-treated poloxamer as described herein is added to a feed or batch-feed cell culture medium.

Commercially available media may be used, including such as, but not limited to, Ham's F10 (Sigma), Minimal Essential Medium ([MEM], Sigma), RPMI-1640 (Sigma), Dulbecco's Modified Eagle's Medium ([DMEM], Sigma), Luria broth (LB), and Terrific broth (TB), and any of these media may be supplemented with any of the media components as detailed herein (e.g., a heat-treated poloxamer). In addition, any of the media described in Ham and Wallace, Meth. Enz., 58:44 (1979), Barnes and Sato, Anal. Biochem., 102:255 (1980), Vijayasankaran et al., *Biomacromolecules.,* 6:605:611 (2005), Patkar et al., *J Biotechnology,* 93:217-229 (2002), U.S. Pat. No. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference in their entirety, may be supplemented with any of the media components as detailed herein (e.g., a heat-treated poloxamer).

Any media provided herein may also be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), surfactants such as poloxamer, and glucose or an equivalent energy source. In some aspects, a cell culture medium provided herein contains proteins derived from a plant or an animal. In some embodiments, a cell culture provided herein is free of proteins derived from a plant or an animal. Any other necessary supplements may also be included at appropriate concentrations that would be known to those skilled in the art.

Cell Viability

In some embodiments, cell viability in a cell culture medium including the heat-treated poloxamer is increased as compared to cell viability in a cell culture medium including untreated poloxamer (or poloxamer before heat treatment). It is a discovery of the present disclosure that preparation of a poloxamer as described herein results in increased cell viability when the heat-treated poloxamer is used in a cell culture medium, as compared when untreated poloxamer is used in the same cell culture medium. Methods for testing cell viability are known in the art. In some embodiments, cell viability is measured as described in detail in the Examples provided herein. In some embodiments, cell viability in a cell culture medium may be measured after about 1 hour, after about 2 hours, or after about 3 hours (e.g., as described below).

As used herein, cell viability is quantified as the percentage of living cells in a solution (i.e., the number of live cells divided by the total number of cells). Any suitable method known in the art may be used to measure cell viability. As cells are either live or dead, cell viability may be determined by quantifying either dead cells or live cells. One suitable method is trypan blue exclusion. In this method, a sample of cells is obtained from a cell culture. A solution of trypan blue is added to the sample. Only non-viable cells take up trypan blue, and these are subsequently stained blue. Therefore, the number of blue cells is counted, subtracted by the total number of cells to yield the number of live cells, and this number is divided by the total number of cells to yield cell viability. Cells may be counted manually, as with a hemacytometer, or automatically, as with, e.g., a Vi-Cell® viability analyzer (Beckman Coulter). Other assays for determining cell viability may include, without limitation, propidium iodide staining, TUNEL, Resazurin, methyl violet, lactate dehydrogenase, fluorescein diacetate hydrolysis, MTT, caspase, and ATP assays.

The effect of a heat-treated poloxamer may be determined, for example, by measuring the cell viability in a cell culture grown in a cell culture medium containing the heat-treated poloxamer and comparing it to the cell viability in a cell culture grown in a cell culture medium containing the same concentration of untreated poloxamer. In some embodiments, a cell culture may be grown in a baffled shake flask. In some embodiments, the use of a heat-treated poloxamer, compared to an untreated poloxamer, increases the cell viability by at least about 10%. In some embodiments, the use of a heat-treated poloxamer, compared to an untreated poloxamer, increases the cell viability by at least about 15%. In some embodiments, the use of a heat-treated poloxamer, compared to an untreated poloxamer, increases the cell viability by at least about 20%. In some embodiments, the use of a heat-treated poloxamer, compared to an untreated poloxamer, increases the cell viability by at least about 25%. In some embodiments, the use of a heat-treated poloxamer, compared to an untreated poloxamer, increases the cell viability by at least about 30%. In some embodiments, the use of a heat-treated poloxamer, compared to an untreated poloxamer, increases the cell viability by at least about 35%. In some embodiments, the use of a heat-treated poloxamer, compared to an untreated poloxamer, increases the cell viability by at least about 40%. In some embodiments, the use of a heat-treated poloxamer, compared to an untreated poloxamer, increases the cell viability by at least about 45%. In some embodiments, the use of a heat-treated poloxamer, compared to an untreated poloxamer, increases the cell viability by at least about 50%.

In some embodiments, cell viability in a cell culture medium comprising a heat-treated poloxamer of the present disclosure is increased by at least 10% as compared to cell viability in a cell culture medium comprising the poloxamer before heat treatment. In some embodiments, the cell viability is increased by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%.

Heat-treated poloxamer may be especially useful for improving the performance of a poloxamer (e.g., a particular lot of a desired poloxamer) that does not yield satisfactory cell viability when added to a cell culture medium. In some embodiments, cell viability in a cell culture medium with untreated poloxamer is below about 80%. In some embodiments, cell viability in a cell culture medium with untreated poloxamer is below about 70%. In some embodiments, cell viability in a cell culture medium with untreated poloxamer is below about 60%. In some embodiments, cell viability in a cell culture medium with untreated poloxamer is below about 50%. In some embodiments, cell viability in a cell culture medium with untreated poloxamer is below about 40%.

Cell Growth and Polypeptide Production

In some embodiments, a cell of the present disclosure (e.g., a cell cultured in a cell culture medium described herein) may contain a polynucleotide of interest (e.g., a polynucleotide encoding a polypeptide of interest, or a polynucleotide of interest per se). In some embodiments, a cell of the present disclosure may be transfected, transformed, or otherwise genetically modified to include a polynucleotide of interest. Methods suitable for transfecting or transforming a variety of cells are widely known in the art. Exemplary references are provided below with respect to polypeptide production; one of skill in the art will appreciate that the methods disclosed therein are not limited to polypeptide production.

Generally the cells are combined (contacted) with any of the cell culture media described herein under one or more conditions that promote any of cell growth, maintenance and/or polynucleotide and/or polypeptide production. Methods of culturing a cell and producing a polypeptide employ a culturing vessel (bioreactor) to contain the cell and cell culture medium. The culturing vessel can be composed of any material that is suitable for culturing cells, including glass, plastic or metal. Typically, the culturing vessel will be at least 1 liter and may be 10, 100, 250, 500, 1000, 2500, 5000, 8000, 10,000, 25,000 liters or more. The culture conditions, such as temperature, pH, and the like, are those previously used with the host cell selected for expression, and will be apparent to the ordinarily skilled artisan. Culturing conditions that may be adjusted during the culturing process include but are not limited to pH and temperature.

A cell culture may be maintained under conditions conducive to the survival, growth, viability (maintenance), and polypeptide production capabilities of the cell culture. The precise conditions will vary depending on the cell type, the organism from which the cell was derived, and the nature and character of the expressed polypeptide. During the polypeptide production phase, the cell culture may optionally be maintained under a second set of culture conditions (as compared to the initial growth phase) conducive to the survival and viability of the cell culture and appropriate for expression of the desired polypeptide.

In certain cases, it may be beneficial or necessary to supplement the cell culture with nutrients or other medium components that have been depleted or metabolized by the cells. For example, it might be advantageous to supplement the cell culture with nutrients or other medium components observed to have been depleted during monitoring of the cell culture. Alternatively or additionally, it may be beneficial or necessary to supplement the cell culture prior to the production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

The cell culture media detailed herein can be used in a method of culturing cells to produce polypeptides, including antibodies. The medium may be used in a method of culturing cells, whether by batch culture, fed batch culture or perfusion culture, and can be used in a method of producing any polypeptide including any aspects or embodiments of the polypeptide as described herein. The polypeptides produced by the methods detailed herein (e.g., of culturing cells and producing polypeptides using a culture medium containing a heat-treated poloxamer of the present disclosure) may be homologous to the host cell, or preferably, may be exogenous, meaning that they are heterologous, i.e., foreign, to the host cell being utilized, such as a human protein produced by a CHO cell, or a yeast polypeptide produced by a mammalian cell. In one variation, the polypeptide is a mammalian polypeptide (such as an antibody) directly secreted into the medium by the host cell. In another variation, the polypeptide is released into the medium by lysis of a cell comprising a polynucleotide encoding the polypeptide.

Any polypeptide that is expressible in a host cell may be produced in accordance with the present disclosure and may be present in the compositions provided. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Methods for producing polypeptides, such as antibodies, in cell culture are well known in the art. Provided herein are non-limiting exemplary methods for producing an antibody (e.g., full length antibodies, antibody fragments and multispecific antibodies) in cell culture. The methods herein can be adapted by one of skill in the art for the production of other proteins, such as protein-based inhibitors. See *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F.M. Ausubel, et al. eds., 2003); *Short Protocols in Molecular Biology* (Ausubel et al., eds., J. Wiley and Sons, 2002); *Current Protocols in Protein Science*, (Horswill et al., 2006); *Antibodies, A Laboratory Manual* (Harlow and Lane, eds., 1988); *Culture of Animal Cells: A Manual of Basic Technique and Specialized Applications* (R.I. Freshney, 6$^{th}$ ed., J. Wiley and Sons, 2010) for generally well understood and commonly employed techniques and procedures for the production of proteins (e.g., therapeutic proteins), which are all incorporated herein by reference in their entirety.

Conditions suitable for the production of polypeptides are known in the art for a variety of host cell types and polypeptides. The culture conditions, such as temperature, pH, and the like, are those previously used with the host cell selected for expression, and will be apparent to the ordinarily skilled artisan.

A cell culture may be agitated or shaken during cell culture in order to increase oxygenation and dispersion of nutrients to the cells. The use of poloxamer may be particularly advantageous in cell cultures that are agitated because of the shear forces that potentially harm the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

Cells

Suitable cells for culturing in a culture medium and producing a polypeptide may include prokaryotic, yeast, or higher eukaryotic (e.g., mammalian) cells. In some embodiments, a mammalian cell is used. In some embodiments, a Chinese Hamster Ovary (CHO) cell is used.

Mammalian cells may be cultured, and propagation of mammalian cells in culture (tissue culture) has become a routine procedure. Examples of mammalian host cell lines may include, without limitation, monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include myeloma cell lines such as NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

In some embodiments, CHO cells may be cultured. CHO cells are well known and routinely used in the art for producing polypeptides in cell culture, for example antibodies. CHO cells may include, but are not limited to, DHFR⁻ CHO cells (Urlaub et al., *Proc. Natl. Acad. Sci. USA* 77:4216 (1980)), e.g., ATCC CRL-9096.

Suitable prokaryotic cells for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and insect cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells. Examples of insect cells may include, without limitation, *Drosophila* cells (e.g., S2 cells), *Trichoplusia ni* cells (e.g., High Five™ cells), and *Spodoptera frugiperda* cells (e.g., Sf21 or Sf9 cells).

Plant cell cultures of cotton, corn, potato, soybean, petunia, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Antibody Production

In some embodiments, the cell cultured in a cell culture medium containing a heat-treated poloxamer is used to produce an antibody.

In some embodiments, the antibody is a monoclonal antibody. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/ 34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661, 016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995). In some embodiments, the antibody produced by the methods described herein is a humanized antibody, a chimeric antibody, a human antibody, a library-derived antibody, or a multispecific antibody.

Antibodies may be produced using recombinant methods, for example in the production of an antibody using CHO cells. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Antibodies can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In some embodiments, the antibody described herein is an antigen-binding fragment thereof. Examples of antigen-binding fragment include Fab, Fab', F(ab')$_2$, and Fv fragments; diabodies; linear antibodies; single-chain antibody molecules; and multispecific antibodies formed from antibody fragments. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known. "Fv" is the minimum antibody fragment which contains a complete antigen-binding site. "Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315. Many of the methods for purifying an antibody described above may be suitably adapted for purifying an antigen-binding antibody fragment.

In general, various methodologies for preparing antibodies for use in research, testing, and clinical are well-established in the art, consistent with the above-described methodologies and/or as deemed appropriate by one skilled in the art for a particular antibody of interest.

EXAMPLES

The invention will be more fully understood by reference to the following examples. The examples should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Heat Treatment Improves Poloxamer Performance for Cell Culture

Poloxamer is commonly used in cell culture as a surfactant that protects cells from sparging and/or bubble-related damage. Unfortunately, lot-to-lot variability undermines its effectiveness and results in reductions in recombinant product yield. For example, a bad lot of poloxamer reduces cell viability and may cause a decrease in product titer of up to 45%. After an extensive series of investigations, it was found that bad poloxamer lots were the source of significant reductions in product yield and subsequent financial losses in industrial protein production. Therefore, methods to improve poloxamer performance would be highly beneficial.

Surprisingly, it has been found that a single heat treatment is able to increase poloxamer performance in cell culture. Importantly, this heat treatment not only improves the performance of bad poloxamer lots, but it is also able to further enhance the performance of good lots as well. Describe herein are methods for treating poloxamer to improve its performance as a cell culture supplement.

Methods

Poloxamer Treatment 15 g of poloxamer 188 (PLURONIC® F 68 NF Prill Poloxamer 188, BASF) were heated on a standard stir plate for 10-12 minutes. Heating was stopped when the poloxamer reached a temperature of 86-91° C. Poloxamer was then cooled at room temperature, 2-8° C., or −72° C. for approximately 20 minutes. Solid poloxamer was then flaked off and added to cell culture medium for testing.

Cell Culture Testing Model

Poloxamer 188, heat treated as described above, was added to standard, serum-free, CHO cell medium at a final concentration of 1 g/L. CHO cells were grown at 37° C. in 25-75 mL cell culture medium in 250 mL baffled shake flasks at a concentration of $1.5 \times 10^6$ cells/mL in 5% $CO_2$. During cell culture, flasks were rotated on an orbital shaker between 250 and 350 rpm. The use baffled shake flasks created a large amount of entrained bubbles in the cultures. Cell viability was measured by trypan blue exclusion using a Vi-Cell® viability analyzer (Beckman Coulter). 300 μL of cell culture was sampled, and the percentage of cell viability was calculated by dividing the number of viable cells (i.e., those that did not take up trypan blue) by the total number of cells in the sample.

Results

A simple screening model was developed for simulating the effect of poloxamer on cell culture viability at a laboratory, rather than industrial, scale. Briefly, CHO cells were grown in 250 mL flasks as described above. In order to maximize the difference in cell viability produced by good and bad lots of poloxamer, volume of cell culture medium and shaking speed were tested. Cells were grown in 25, 50, or 75 mL medium and shaken on an orbital shaker platform at 250, 300, or 350 rpm. It was found that the volume of medium had no effect on $\Delta_{viability}$ (i.e., the difference in cell viability, as a percentage, between a known good lot and a known bad lot of poloxamer), but higher shaking speeds showed an increase in $\Delta_{viability}$.

As shown in FIG. 1, it was found that heat-treating poloxamer (see Methods) significantly improves the performance of poloxamer in cell culture. A variety of poloxamer lots were tested for their effect on cell viability using the above screening model. Some lots were known to perform well, and others were suspected to be poorly performing. For each lot, untreated and heat-treated (HT) batches were added to the cell culture medium for testing. Compared to untreated poloxamer, heat-treated poloxamer was found to improve cell viability in all lots tested (FIG. 1). In some cases, heat-treated poloxamer was able to double viability, from 45% to nearly 90%. Importantly, heat-treated poloxamer was able to improve viability for lots that already demonstrated high performance (see, e.g., "Good 4" in FIG. 1).

These results demonstrate that heat treatment of poloxamer is able to improve its effect on viability in cell culture. Heat treatment is able to dramatically improve the performance of bad poloxamer lots and even further enhance the performance of good lots, suggesting implementation of poloxamer heat treatment may significantly reduce the problem of poloxamer lot variability.

Example 2: Poloxamer Heat Treatment Measured with an RTD Thermometer

The experiments described in Example 1 were conducted on a hot plate. These experiments involved heating poloxamer to approximately 80-100° C. (measured by RTD) over the course of 10 minutes. These experiments were repeated with the addition of a sample heated to above 100° C. (i.e., 124° C.).

Methods

Poloxamer 188 Manufacturers and Lots

Poloxamer 188 material was used. Identifiers and associated cell culture performance (determined by performance in the High Shear Shake Flask Test, HSSF) are listed in Table 1.

TABLE 1

Identifiers (used to refer to lot throughout the subsequent examples) and associated cell culture performance from HSSF data.

| Identifier | Cell Culture Performance |
|---|---|
| G | Bad |
| D | Good |
| H | Bad |
| B | Bad |
| C | Bad |
| F | Bad |
| E | Marginal |
| A | Good |

Heat Treatment Methods

To evaluate the poloxamer heat treatment process, several methods of heat treatment were evaluated: heating on a hot plate, in an oven, or in an autoclave.

Hot Plate

Five to fifteen grams of poloxamer was placed in a glass beaker (100-400 mL) and heated on a hot plate with continuous stirring. Temperature of the poloxamer was measured using a thermocouple (Kaye 731 Thermocouple) or a resistance temperature detector (RTD) (Fluke 5627A-12 Precision RTD Probe). Poloxamer was heated until it reached the target temperature (approximately five to ten minutes) and then was immediately removed from heat. The molten poloxamer was allowed to cool at room temperature.

Oven

Five grams of poloxamer was weighed out in a 20 mL scintillation glass vial. A thermocouple was secured in the vial such that the tip was immersed in the dry poloxamer. The poloxamer and thermocouple were then placed in an oven (Yamato ADP 21 Vacuum Drying Oven) already at the target temperature. Unless otherwise specified, ovens were operated without the vacuum function (at atmospheric pressure). The poloxamer was allowed to reach target temperature (+/−3° C. as measured by the thermocouple), and the time at which the poloxamer reached this target temperature was marked as time=0. After the desired incubation time, a slight vacuum was applied for 10-30 seconds to siphon off any volatiles released into the oven. After venting, the glass vial was removed from the oven and allowed to cool at room temperature (uncapped).

CHO Cell Culture and Media

Standard, serum-free, CHO cell medium was used for all experiments, with one notable exception: Pluronic F68 was omitted from the medium. To support this study, two CHO cell line thaws were maintained in a seed train bioreactor (STB).

High Shear Cell Culture Shake Flask Method

Addition of Poloxamer Samples to Cell Culture Media

Media was prepared by aliquoting 250 mL of standard, serum-free, CHO cell medium (without poloxamer) per sample into PETG containers and adding 0.25 grams of poloxamer sample to each aliquot. Media was agitated for at least 5 minutes at 150 rpm in order to thoroughly dissolve poloxamer in media. Media was then vacuum-filtered in a biosafety cabinet (BSC) using 0.22 μm PES filter units. Media was stored at 37° C. for use within 24 hours.

Media Exchange and Cell Culture Assay

Cell culture samples were transferred into 50 mL Falcon tubes such that each aliquot contained approximately 7.5× 10E7 cells. The cells were centrifuged for 10 minutes at 830×g to form a pellet. The supernatant was removed and cells were re-suspended in media containing poloxamer samples to test, and then transferred into 250 mL vented baffled shake flasks. The initial total cell density (TCD) and viability were measured using a NOVA Flex after shaking flasks at 150 rpm for a few minutes to evenly distribute cells. Shake flasks were then placed in an incubator at 5% $CO_2$, 80% humidity, and 37° C. and shaken at 300 rpm for 3 hours. TCD and viability measurements were taken after 1 hour, 2 hours, and 3 hours of incubation and compared to original TCD and viability.

Results

Samples of a good lot of poloxamer (A) and two bad lots (B and C) were heat treated to approximately 100° C. An additional sample of C was heat treated to 124° C. Post heat treatment, samples were tested in the HSSF test.

Figure 2:
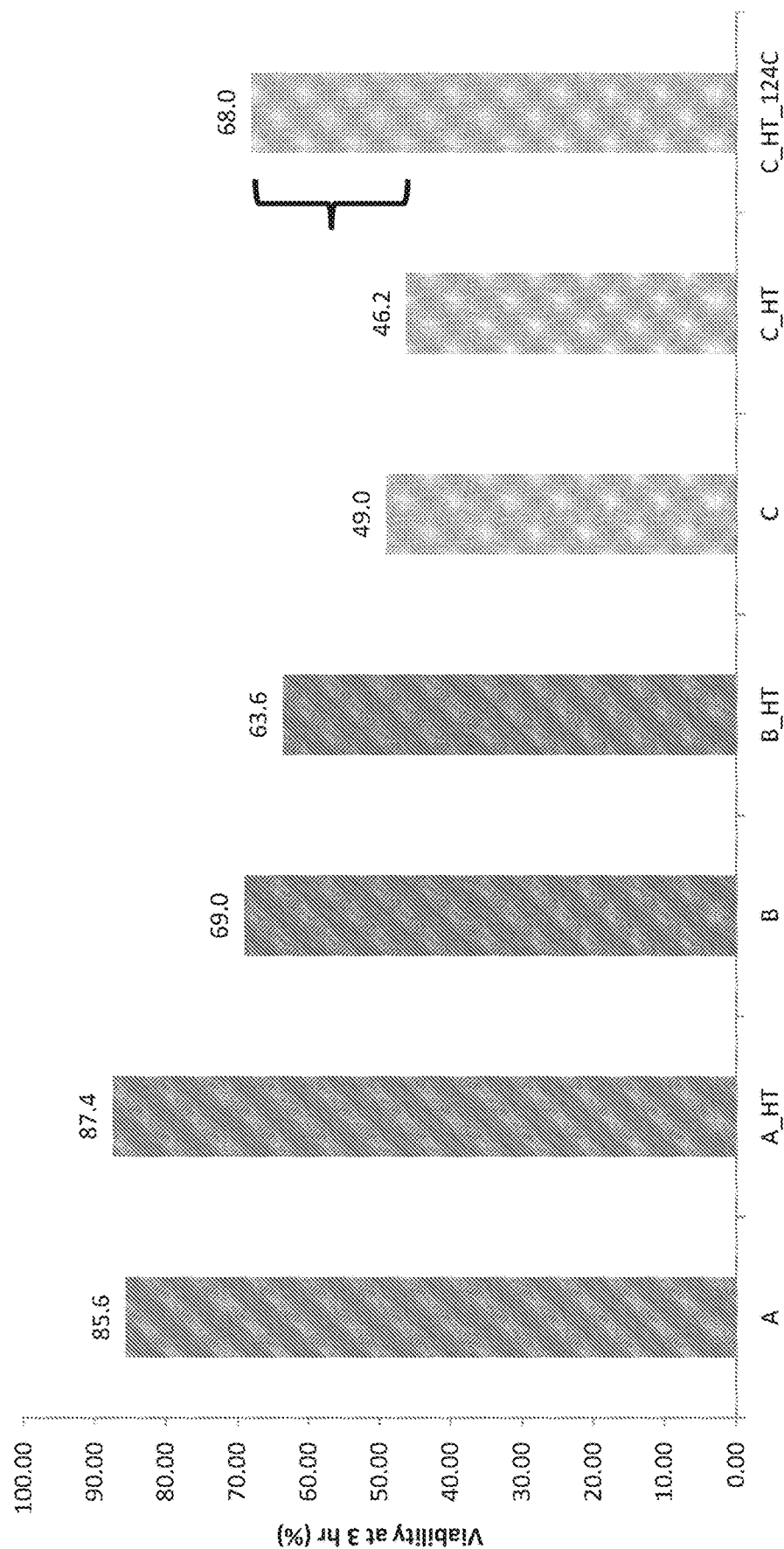
FIG. 2 shows cell viability (%) in a high shear shake flask model (HSSF) test for untreated and heat treated (_HT) poloxamer samples A, B, and C (see also Table 2).

All poloxamer samples treated to 100° C. (as measured by RTD) showed no improvement over untreated material of the same lot (FIG. 2). However, C heat treated to 124° C. demonstrated a 19% increase in final viability compared to untreated C. Additionally, the overall change in viability (i.e., final viability %, $V_f$, minus initial viability %, $V_0$) for the heat treated C was −27.4%, a 21% increase compared to untreated C (Table 2).

TABLE 2

Heat treated poloxamer samples, conditions, viability improvement over untreated lot, and final viability in the HSSF test.

| Sample Description | Sample ID | Viability improvement over untreated lot @ 3 hrs | Viability @ 3 hr (%) |
|---|---|---|---|
| Good lot, untreated | A | 0.0 | 85.6 |
| Good lot, heat treated | A_HT | 1.8 | 87.4 |
| Bad lot (B), untreated | B | 0.0 | 69.0 |
| Bad lot (B), heat treated to 100 C. | B_HT | −5.4 | 63.6 |
| Bad lot (C), untreated | C | 0.0 | 49.0 |
| Bad lot (C), heat treated to 100 C. | C_HT | −2.8 | 46.2 |
| Bad lot (C), heat treated to 124 C. | C_HT_124 C. | 21.8 | 68.0 |

High shear shake flask model run with N = 1

These results confirmed that heat treatment improved poloxamer performance in cell culture and gave a preliminary indication of effective temperature and treatment duration. However, these results suggest that temperatures higher than 100° C. may be more effective in heat-treating poloxamer for cell culture. It is thought that differences in temperature measurement (e.g., the type of thermometer used to measure the temperature of poloxamer) may result in different effective ranges for poloxamer heat treatment (see Example 8 for further data and discussion).

Example 3: Transferring Heat Treatment to Ovens

A bench top drying oven was used as an alternative heating mechanism, which provided temperature control and reproducibility. Additionally, the vacuum function allowed the fumes released by the melting poloxamer to be siphoned out of the oven prior to opening it and removing the heat treated poloxamer. Oven experiments were performed according to the methods described in Example 2.

Figure 3:
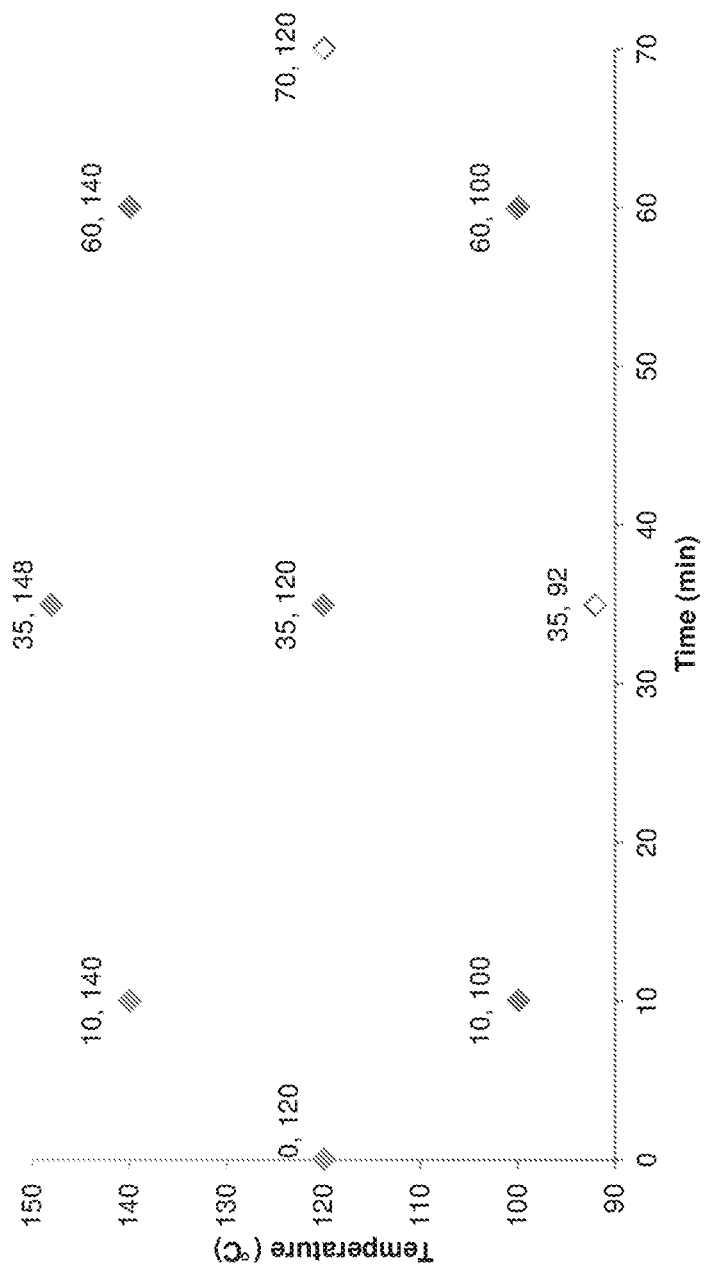
FIG. 3 shows the response surface design of conditions tested in ovens. Each condition is labeled in the format "time, temperature." Conditions marked with '♦' were tested in HSSF. Conditions marked with '◇' were prepared in ovens but not tested in HSSF. Temperature (in ° C.) represents the set temperature of the oven, while time (in min) represents the time the poloxamer sample was in the oven.

Initial experiments in the oven used a response surface design in order to test a large range of conditions with minimal number of required samples (FIG. 3). The temperature ranged from 92-148° C., with incubation times from 10-120 minutes. Samples of a bad lot (C) were heat treated at specified conditions in an oven. Resulting samples were then tested in the HSSF model to determine improvement in cell culture performance.

Figure 4:
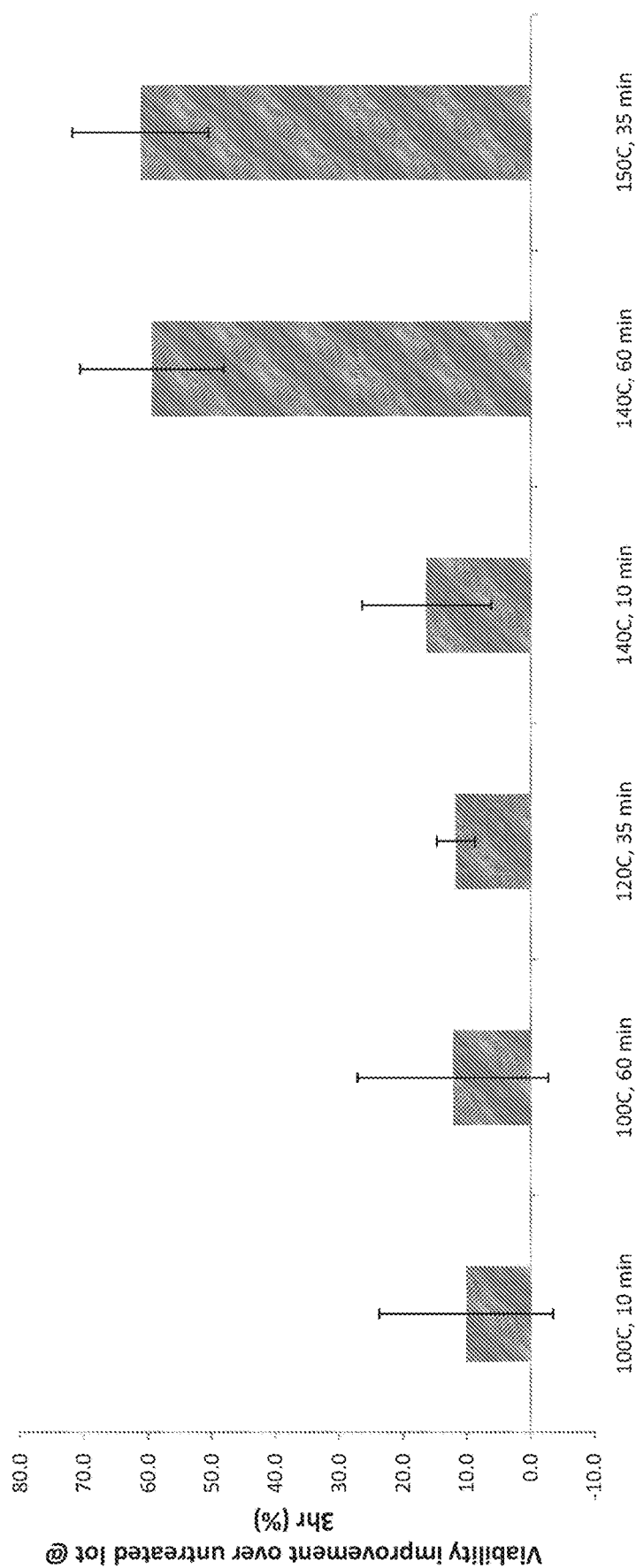
FIG. 4 shows the improvement in cell viability (%) ($Vf_{(treated)}-Vf_{(untreated)}$) for samples of C poloxamer heat treated in ovens under the indicated conditions, compared to positive ("Good lot") and negative ("Untreated bad lot") controls (D and C, respectively). Error bars depict one standard deviation.

Poor performing poloxamer heated in an oven at 140° C. for 60 minutes and 150° C. for 35 minutes showed substantial increases in final viability, equivalent to that of the positive control in the HSSF test (FIG. 4 and Table 3).

TABLE 3

Viability for poloxamer heated in an oven.

| Sample ID | Averaged Viability @ 3 hr | Standard Deviation (SD)* | Averaged Viability improvement over untreated lot @ 3 hrs | Viability Improvement Standard Deviation (SD)* |
|---|---|---|---|---|
| Untreated bad lot (C) | 30.4 | 11.1 | 0.0 | 0.0 |
| Positive Control (D) | 88.4 | 2.5 | 58.1 | 13.6 |

TABLE 3-continued

Viability for poloxamer heated in an oven.

| Sample ID | Averaged Viability @ 3 hr | Standard Deviation (SD)* | Averaged Viability improvement over untreated lot @ 3 hrs | Viability Improvement Standard Deviation (SD)* |
|---|---|---|---|---|
| C_100 C., 10 min | 40.5 | 3.9 | 10.1 | 15.0 |
| C_100 C., 60 min | 42.6 | 8.1 | 12.2 | 3.0 |
| C_120 C., 35 min | 42.1 | 1.0 | 11.8 | 10.1 |
| C_140 C., 10 min | 46.7 | 0.1 | 16.4 | 11.2 |
| C_140 C., 60 min | 89.7 | 0.4 | 59.4 | 10.7 |
| C_150 C., 35 min | 91.6 | 0.5 | 61.2 | 11.6 |

*HSSF model run in duplicates

However, in these experiments, poloxamer heat treated at conditions below 140° C. and/or for less than 60 minutes showed no improvement in performance. These data indicated that the minimum temperature of heat treatment to improve poloxamer performance was approximately 140° C. at the durations of time tested. More extensive tests of temperature and duration of heating are described below, e.g., in Example 5.

Example 4: Oven Heat Treatment DOE

The primary response surface map for heat treatment conditions in ovens indicated the minimum temperature for effective heat treatment under the conditions tested was approximately 140° C. The full design of experiments (DOE) was performed in ovens according to the methods of Example 2 to determine the working range by going to very high temperatures and long incubation times. The maximum temperature tested was 185° C. and the maximum incubation time tested for each temperature was 120 minutes. A bad lot of poloxamer (G) was treated and tested in six-sample blocks which were segmented using a Latin Square design. In total, three sample blocks and an additional six samples of conditions of interest were treated (Table 4). These samples were then tested in the HSSF test to determine cell culture performance.

TABLE 4

Heat treatment conditions evaluated in the full DOE in ovens.
Temperatures ranged from 110-185° C.;
duration ranged from 1-120 min. Boxes marked
with a letter (corresponding to blocks in Table 5) indicate
treatment conditions that were tested, as listed in Table 5.

| Temperature (° C.) | Time (min) | | | | | |
|---|---|---|---|---|---|---|
|  | 1 | 5 | 10 | 30 | 60 | 120 |
| 110 | A |  |  | D | X | F |
| 125 |  |  | D |  | F | A |
| 140 | F | A | X | X | D | X |
| 155 | X | D |  | F | A |  |
| 170 |  | F | A |  |  | D |
| 185 | D |  | F | A |  | X |

Figure 5:
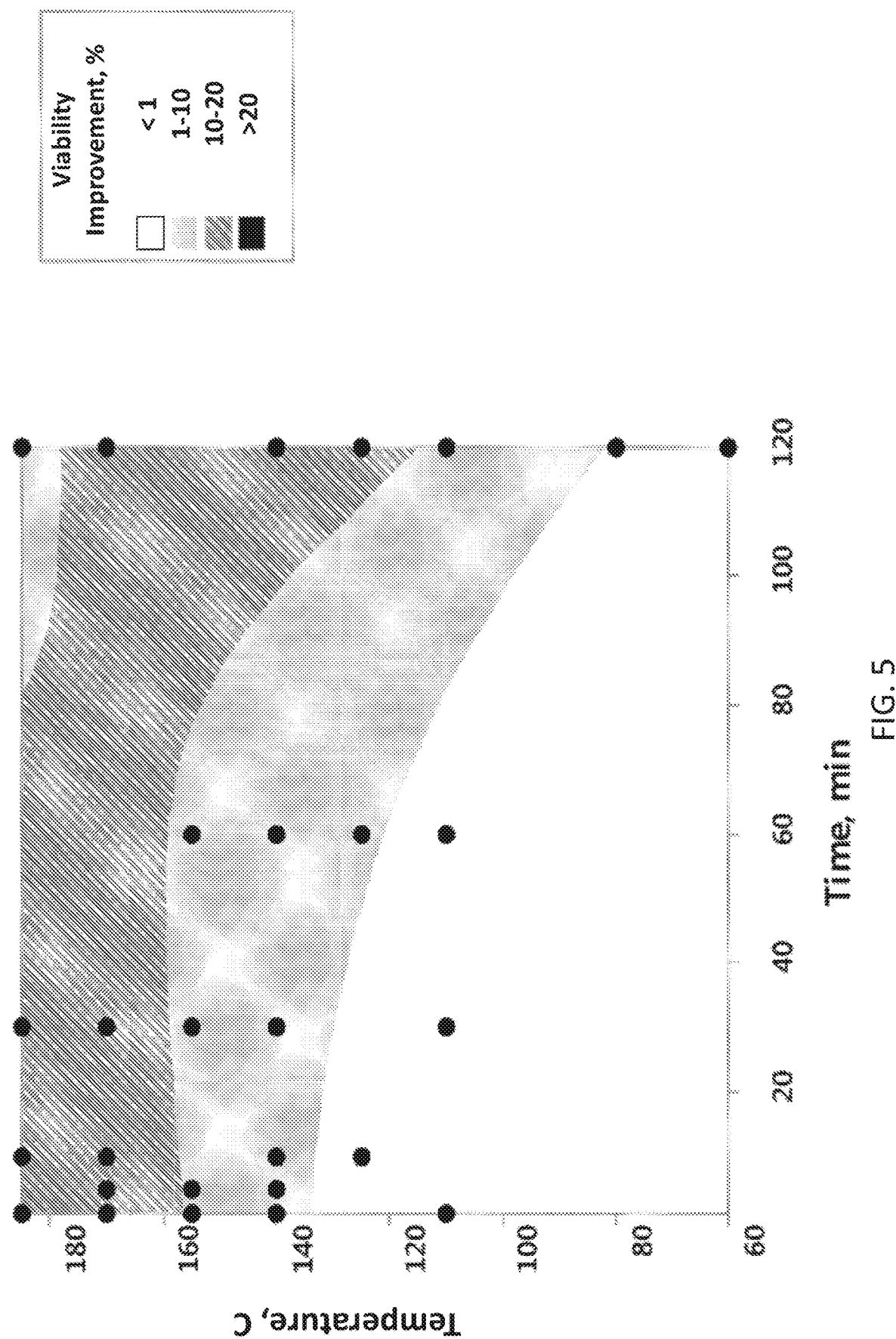
FIG. 5 shows a contour plot from a full design of experiments (DOE) exploring effects of different heat treatment conditions on poloxamer performance in cell culture. Viability improvement ($Vf_{(treated)}-Vf_{(untreated)}$) in the HSSF test is shown as a function of time and temperature. Dots indicate sample conditions tested.

DOE raw data is shown in Table 5. The full DOE results, when mapped on a contour plot, illustrated the large working range of heat treatment conditions that improve poloxamer performance (FIG. 5).

TABLE 5

Raw data from the full DOE experiment.

| Lot Number | Time, Min | Temperature, C. | Block | Viability @ 3 hrs | Viability Improvement (over untreated control average) % |
|---|---|---|---|---|---|
| G | 1 | 110 | A | 74.9 | −4.8 |
| G | 5 | 140 | A | 77.1 | −2.6 |
| G | 10 | 170 | A | 88.9 | 9.2 |
| G | 30 | 185 | A | 89.5 | 9.8 |
| G | 60 | 155 | A | 88.7 | 9.0 |
| G | 120 | 125 | A | 82.3 | 2.6 |
| G | 10 | 140 | B | 91.3 | 11.6 |
| G | 1 | 155 | C | 93.6 | 13.9 |
| G | 30 | 140 | C | 95.5 | 15.8 |
| G | 120 | 185 | C | 95.9 | 16.2 |
| G | 1 | 185 | D | 93.9 | 14.2 |
| G | 5 | 155 | D | 92.6 | 12.9 |
| G | 10 | 125 | D | 73.4 | −6.3 |
| G | 30 | 110 | D | 51.9 | −27.8 |
| G | 60 | 140 | D | 93.7 | 14.0 |
| G | 120 | 170 | D | 82.6 | 2.9 |
| G | 60 | 110 | E | 82.1 | 2.4 |
| G | 120 | 140 | E | 95.9 | 16.2 |
| G | 1 | 140 | F | 68.5 | −11.2 |
| G | 5 | 170 | F | 94.5 | 14.8 |
| G | 10 | 185 | F | 95.6 | 15.9 |
| G | 30 | 155 | F | 95.2 | 15.5 |
| G | 60 | 125 | F | 68.2 | −11.5 |
| G | 120 | 110 | F | 94.8 | 15.1 |

Samples heat treated at or above 155° C. for all incubation times resulted in drastic improvements in cell culture performance. In the HSSF test, these samples had changes in viability less than 10% after 3 hr. At 140° C., heat treatment was not effective until incubation time was at or above 30 minutes. Additionally, the lowest temperatures tested, 125° C. and 110° C., were not effective until samples were incubated for 2 hours.

Example 5: Heat Treatment Robustness and Reproducibility

In order to demonstrate the reproducibility and robustness of the heat treatment design space illustrated in FIG. 5, key treatment conditions from the full DOE were replicated using additional lots of poloxamer according to the methods described in Example 2. Two of these conditions were duplicated in order to address reproducibility. Selected conditions fell inside or on the edge of the working range. In total, three bad lots were treated (including G, which was previously used for the DOE) (Table 6). To ensure that heat treatment would not be detrimental if performed on a good lot, one good lot was also treated (E).

TABLE 6

Number of replicates for key heat treatment conditions
tested across four poloxamer lots.

| Temperature | Time | Bad lot #1 (G) | Bad lot #2 (H) | Bad lot #3 (F) | Good lot (E) |
|---|---|---|---|---|---|
| 170 C. | 1 min | 1 | 1 | 1 | 1 |
|  | 30 min | 1 | 1 | 1 | 1 |
| 155 C. | 1 min | 3 | 2 | 2 | 2 |
|  | 30 min | 2 | 1 | 1 | 1 |

TABLE 6-continued

Number of replicates for key heat treatment conditions tested across four poloxamer lots.

| Temperature | Time | Bad lot #1 (G) | Bad lot #2 (H) | Bad lot #3 (F) | Good lot (E) |
|---|---|---|---|---|---|
| 140 C. | 1 min | 2 | 1 | 1 | 1 |
|  | 30 min | 3 | 2 | 2 | 2 |

Figure 6:
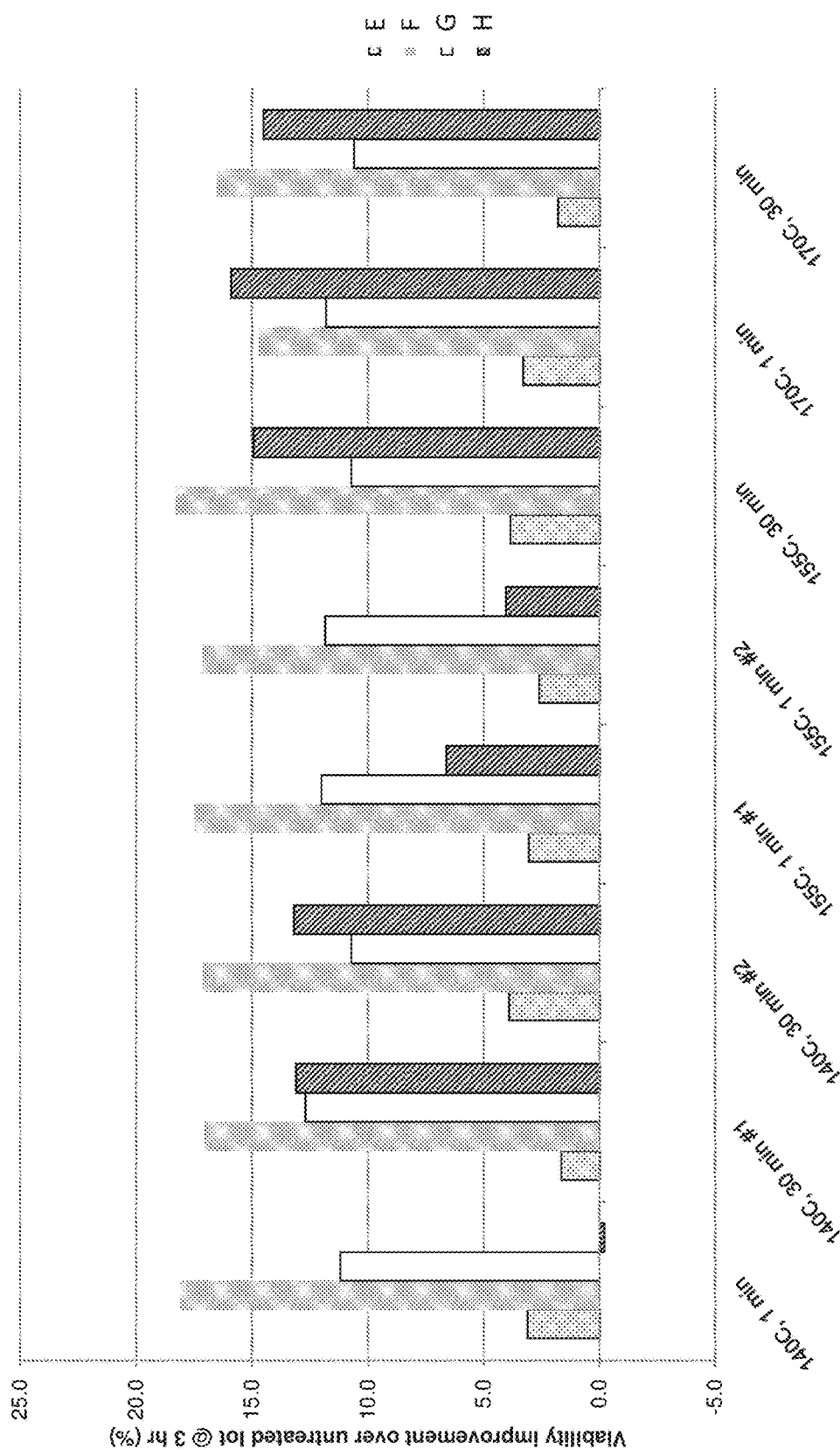
FIG. 6 shows improvement in cell viability (%) ($Vf_{(treated)}-Vf_{(untreated)}$) in a HSSF test for poloxamer samples from three bad lots (H, F, and G) and one good lot (E) heat treated under the indicated conditions.

The HSSF test results for the repeated treatment conditions were highly comparable to results from the original DOE (Tables 7 and 8); however, there was observable variability in optimal heat treatment conditions across bad lots (FIG. 6).

TABLE 7

Final cell viability for heat treatment conditions tested in the HSSF test on four lots of poloxamer E (good lot), F (bad lot), H (bad lot), and G (bad lot used in full DOE experiments).

| Sample | E | F | G | H |
|---|---|---|---|---|
| Untreated | 92.2 | 72.7 | 78.8 | 77.5 |
| 140 C., 30 min #1 | 93.8 | 89.8 | 91.5 | 77.3 |
| 140 C., 30 min #2 | 96.1 | 89.8 | 89.5 | 90.6 |
| 140 C., 1 min | 95.3 | 90.8 | 90.0 | 90.7 |
| 155 C., 1 min #1 | 95.2 | 90.2 | 90.8 | 84.1 |
| 155 C., 1 min #2 | 94.8 | 89.9 | 90.7 | 81.5 |
| 155 C., 30 min | 96.0 | 91.0 | 89.5 | 92.4 |
| 170 C., 1 min | 95.5 | 87.4 | 90.6 | 93.4 |
| 170 C., 30 min | 94.0 | 89.2 | 89.4 | 92.0 |

TABLE 8

Change in cell viability ($Vf_{(treated)}-Vf_{(untreated)}$) in HSSF test for heat treatment conditions tested on four different poloxamer lots: E (good lot), F (bad lot), H (bad lot), and G (bad lot used in full DOE experiments). Viability improvement over untreated lot @ 3 hr (%)

| | Lots | | | |
|---|---|---|---|---|
| Sample | E | F | G | H |
| 140 C., 1 min | 3.1 | 18.1 | 11.2 | -0.2 |
| 140 C., 30 min #1 | 1.6 | 17.1 | 12.7 | 13.1 |
| 140 C., 30 min #2 | 3.9 | 17.1 | 10.7 | 13.2 |
| 155 C., 1 min #1 | 3.1 | 17.5 | 12.0 | 6.6 |
| 155 C., 1 min #2 | 2.6 | 17.2 | 11.9 | 4.1 |
| 155 C., 30 min | 3.8 | 18.3 | 10.7 | 15.0 |
| 170 C., 1 min | 3.3 | 14.7 | 11.8 | 15.9 |
| 170 C., 30 min | 1.8 | 16.5 | 10.6 | 14.5 |

High shear shake flask model run with N = 1

Lots G and F, when treated at 155° C. for 1 min or 140° C. for 1 minute, demonstrated a significant increase in cell culture performance. However, lot H showed no improvement with treatment at 140° C. for 1 minute, and only marginal (<10%) improvement with treatment at 155° C. for 1 min. All other treatment conditions for this lot showed significant improvement in cell culture. These results demonstrate that lots have slight differences in minimum temperature and incubation time of heat treatment.

Example 6: Evaluation of Lower Temperatures and Long Duration

The heat treatment conditions described in Examples 2-5 were well above the melting point of poloxamer. To determine if temperatures only slightly above the melting point of poloxamer (~50° C.) could have an effect on cell culture viability, samples of two bad lots of poloxamer (H and G) were treated in ovens at 60° C. and 80° C. for 120 minutes and then tested in the HSSF method according to Example 2.

Figure 7:
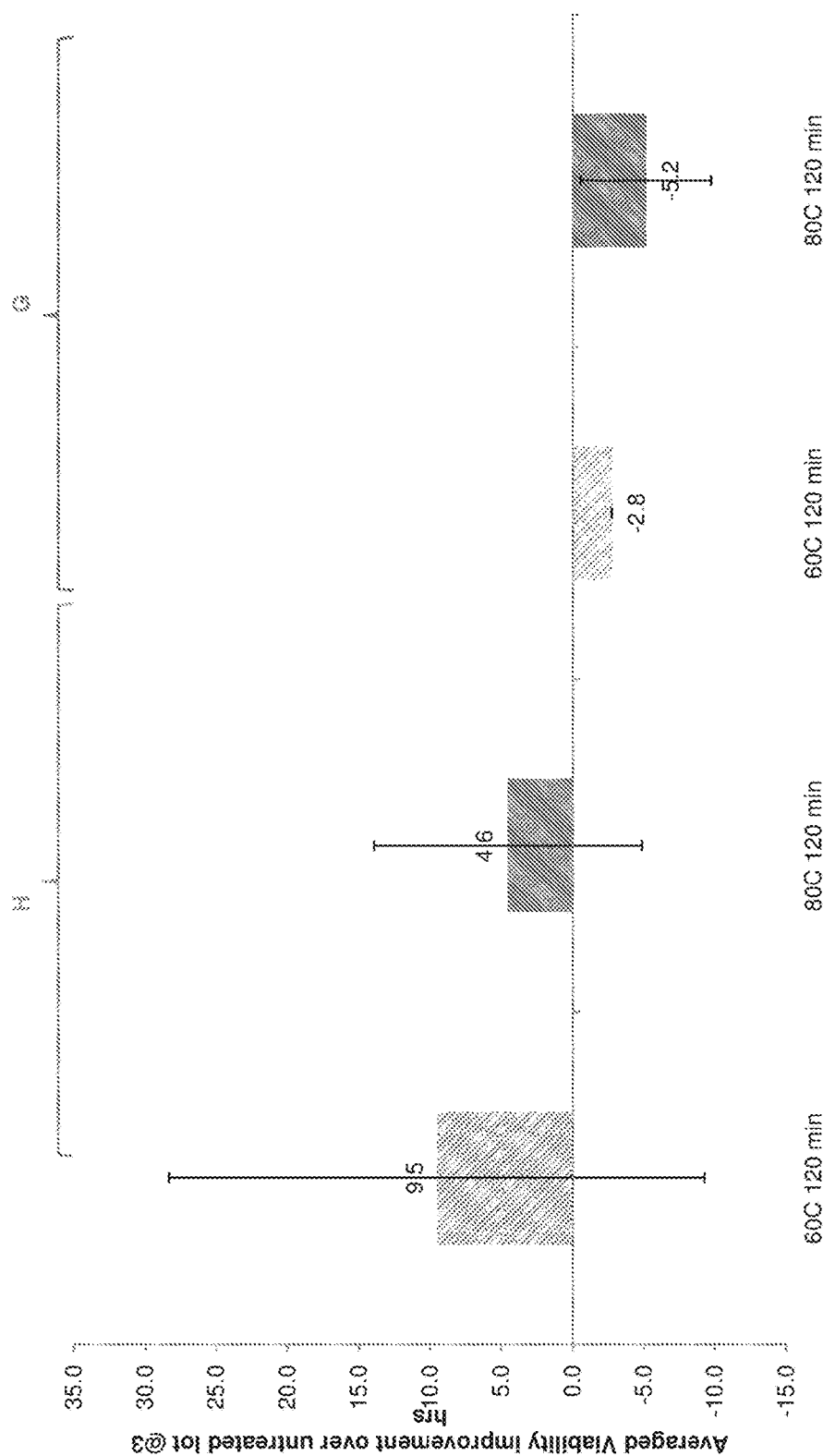
FIG. 7 shows a comparison of improvement in cell viability (%) ($Vf_{(treated)}-Vf_{(untreated)}$) for bad poloxamer lots (H and G) treated at low temperatures (60-80° C.) for a long duration (120 min). *HSSF model run in duplicates.

Results for the heat treated samples demonstrated no significant improvement in performance compared with untreated poloxamer, regardless of temperature (FIG. 7). Without wishing to be bound to theory, it is hypothesized that longer incubation times may be required for these lower temperatures to yield improved poloxamer.

Example 7: Heat Treatment in Vacuum

To determine the impact of oxygen on poloxamer heat treatment, samples of two bad poloxamer lots (H and G) were heat treated to 140° C. while under a slight vacuum in the oven according to the methods in Example 2. Rather than removing samples from the vacuum after a certain incubation time, the poloxamer was cooled in the oven under vacuum down to room temperature to ensure that there was no external oxygen exposure while the poloxamer was at the target temperature.

TABLE 9

Poloxamer heat treatment conditions and HSSF results for samples tested in a vacuum.

| Sample ID | Averaged Viability @ 3 hr | Standard Deviation (SD)* | Averaged Viability improvement over untreated lot @ 3 hrs | Viability Improvement Standard Deviation (SD)* |
|---|---|---|---|---|
| H (Untreated) | 58.8 | -37.5 | 0.0 | 0.0 |
| H_60 C. 120 min | 68.3 | 0.0 | 9.5 | 18.8 |
| H_80 C. 120 min | 63.4 | 9.4 | 4.6 | 9.4 |
| G (Untreated) | 80.0 | -16.5 | 0.0 | 0.0 |
| G_60 C. 120 min | 77.2 | 2.5 | -2.8 | 4.6 |
| G_80 C. 120 min | 74.8 | 0.1 | -5.2 | 7.3 |

*High shear shake flask model run with N = 2

Figure 8:
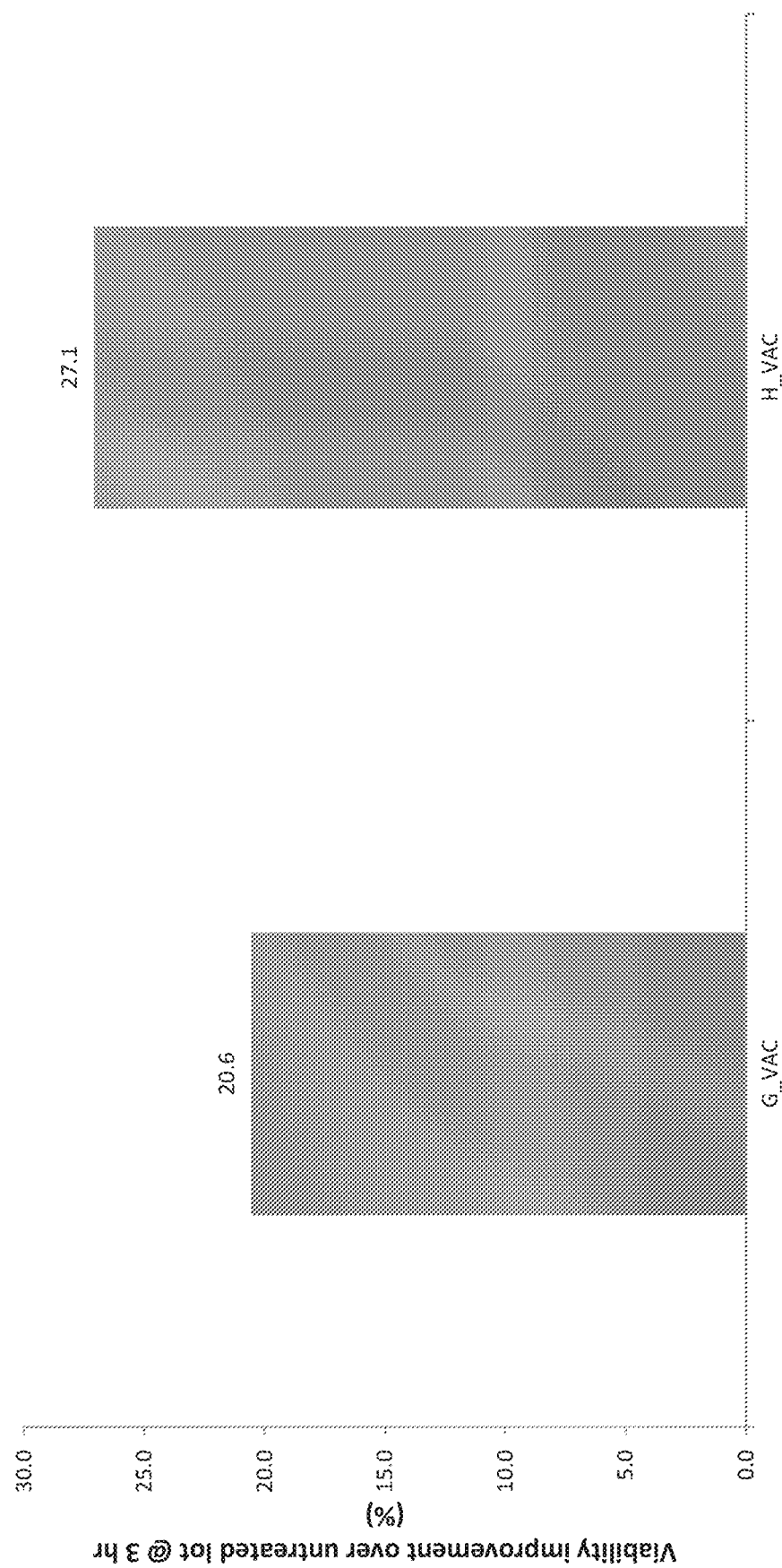
FIG. 8 shows the improvement in cell viability (%) ($Vf_{(treated)}-Vf_{(untreated)}$) in a HSSF test for poloxamer samples (H and G) heat treated under vacuum conditions, as compared to untreated.

Poloxamer treated in a vacuum demonstrated a significant improvement (>20% increase in final viability) over untreated poloxamer in cell culture (FIG. 8, Table 9). These results demonstrate that external oxygen exposure during poloxamer heat treatment may not be required to produce improved poloxamer.

Example 8: Temperature Measurement Using an RTD Versus a Wire Thermocouple

Previous data supported a temperature range of 80-100° C. for the heat treatment process. However, the full DOE (e.g., as shown in FIG. 5) supported an operating range at or above 140° C.

An experiment was conducted examining the two different thermometers used to measure poloxamer temperature during heat treatment. The experiments described in Example 1 used an RTD, while a wire thermocouple was used in all oven experiments. The RTD used requires an immersion depth of 4" for accurate temperature measurement. Conversely, the wire thermocouple is designed to measure temperature precisely at its tip, enabling it to accurately measure temperature while immersed in only a few millimeters of poloxamer.

A side-by-side comparison was performed while heat treating poloxamer on a hot plate according to the methods in Example 2. The wire thermocouple gave a temperature reading of 152.6° C., whereas the RTD thermometer gave a reading of 81.65° C. Thus, the RTD showed a significant under-measurement of temperature (>70° C.) when compared with the thermocouple. These results demonstrate that different poloxamer temperature readings underlie differences in effective temperature ranges sufficient for producing improved poloxamer.

Example 9: Heating Ramp and Cooling Rate Characterization in Oven

Poloxamer samples, once placed in an oven, do not immediately reach target temperature. The heating and cooling profiles for three temperatures used in the DOE were evaluated in the oven according to the methods in Example 2.

Figure 9:
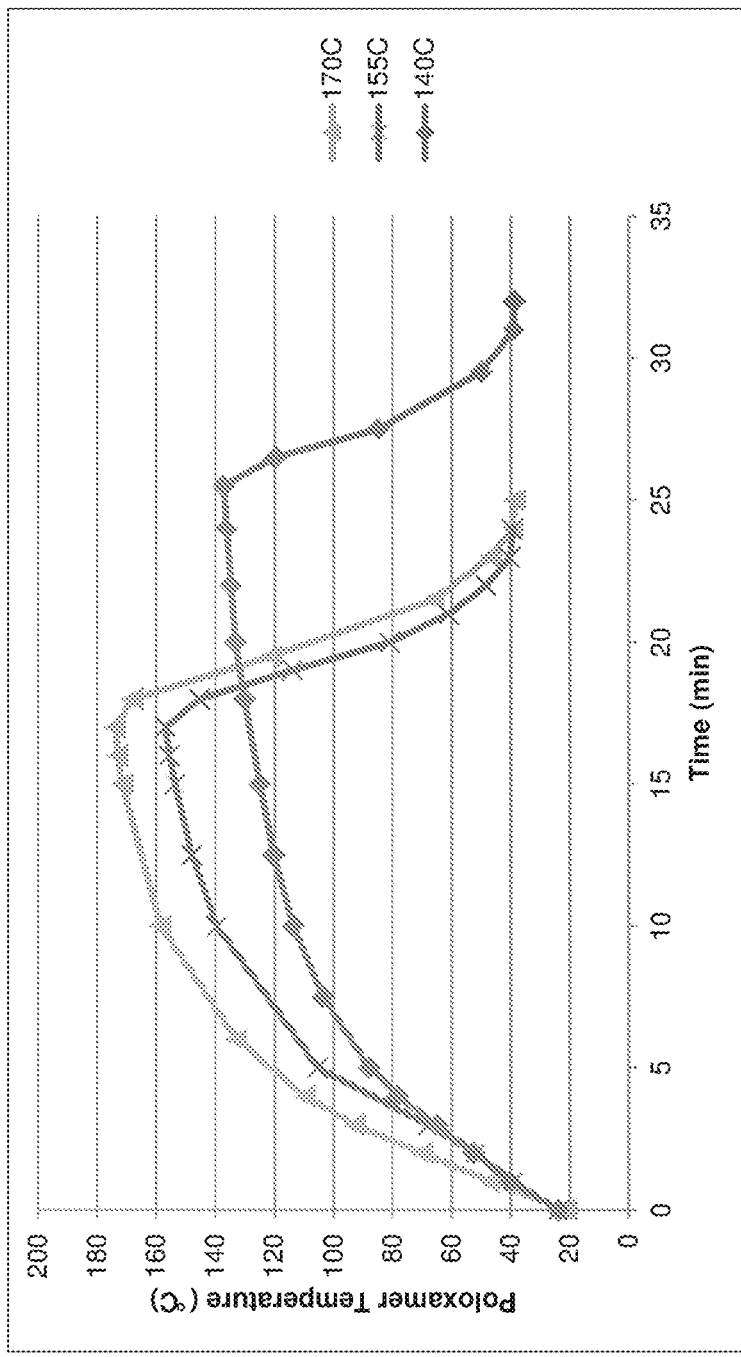
FIG. 9 shows heating and cooling profiles for poloxamer material in ovens. Three temperatures were tested: 140° C., 155° C., and 170° C. Once the temperature readout began to stabilize, material was removed from the oven and cooled at room temperature. Profiles leveled off at 40° C., near the melting point of poloxamer.

Samples took an average of 18 minutes to reach target temperature (+/−3° C.) in the oven with a standard deviation of 5.8 minutes (FIG. 9). Despite the variability in heating times, the cooling rates were relatively similar. The average time for a sample to reach the melting temperature of poloxamer (~40° C.) was 7 minutes, with a standard deviation of 0.8 minutes. Assuming that the cooling profiles are largely linear, the cooling rates for samples heated to 170C, 155C, and 140C were approximately −19° C./min, −19.5° C./min, and −18° C./min, respectively.

Example 10: Statistical Significance of Viability and Poloxamer Heat Treatment

A student's t-test was used to determine the difference between the poloxamer control lots' performance in the HSSF tests and the significance of observed improvements in cell culture performance. All HSSF control results from the oven DOE were included in the data set. For heat treated samples, only samples within the working range were used to calculate the mean change in cell viability post heat treatment. The working range was defined to be conditions where change in viability in the HSSF test was less than 15%.

Treated and untreated poloxamers were compared using a student's t-test ($\alpha$=0.05) to determine statistically significant differences in means. Additionally, results of treated material were compared to the positive control (D) results.

TABLE 10

Mean delta viability ($Vf_{(treated)} - Vf_{(untreated)}$) in the HSSF test for treated and untreated poloxamer material of tested lots.

| Lot Number | Mean Viability @ 3 hr (%), Untreated | Mean Viability @ 3 hr (%), Treated | P value Untreated × Treated |
| --- | --- | --- | --- |
| G | 78.7 | 91.4 | <0.0001* |
| E | 92.2 | 95.1 | 0.2490 |
| F | 79.3 | 89.8 | <0.0006* |
| H | 67.9 | 91.8 | <0.0001* |
| D | 87.8 | — | — |

With an alpha level of 0.05, mean comparisons between untreated bad lots of poloxamer and the positive control lot (D) demonstrated significant differences (Table 10). Post heat treatment, all lots performed significantly better than the positive control lot, with the exception of H, which was comparable. Lot E, a good lot, had a p value>0.05, indicating its performance was not significantly different than the positive control lot. However, heat treated poloxamer from lot E performed significantly better in the HSSF test than the positive control (p value=0.0005), demonstrating that the heat treatment process improved an already acceptable lot.

Figure 10:
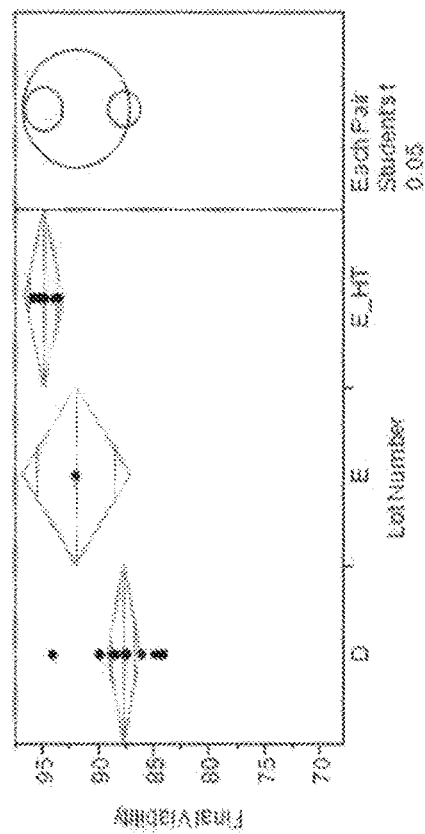
FIG. 10 shows student's t-test results for each lot of heat treated poloxamer compared to the positive control (D) and untreated material. Mean diamonds illustrate 95% confidence intervals (upper and lower points) and mean (center line) for each data set.
Figure 10:
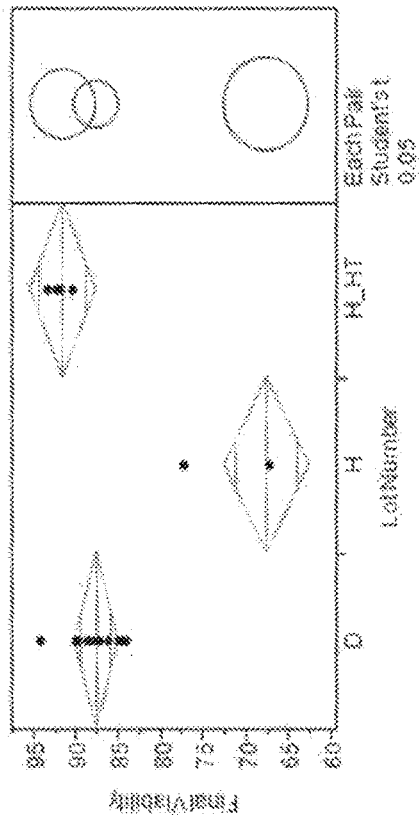
Figure 10:
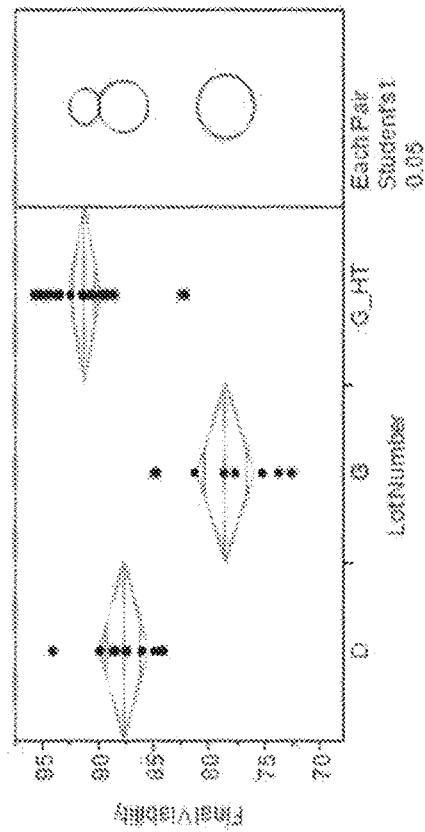
Figure 10:
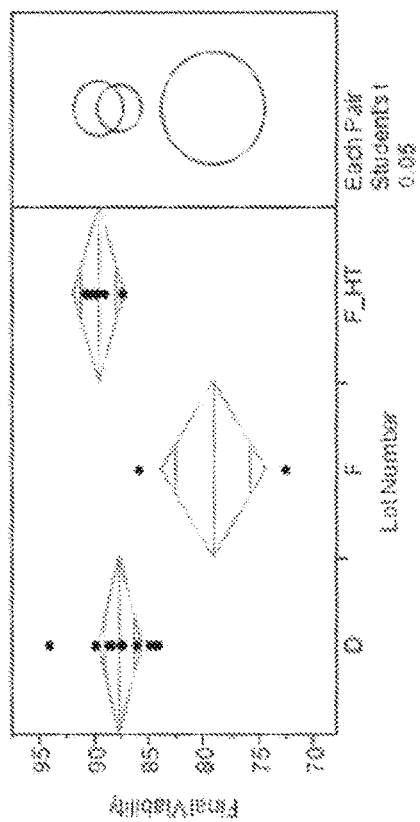

These results are illustrated in FIG. 10, which displays treated and untreated results of each lot compared to the overall positive control data set. For example, FIG. 10 illustrates that for bad lot G, the untreated G, the positive control good lot D, and the heat-treated G were all statistically distinguishable, with the heat-treated G lot showing significantly improved viability, as compared either to the positive control good lot (D) or the untreated G bad lot.

Based on this analysis, cases where the heat treatment process was deemed successful demonstrated an 18% improvement over untreated material. Furthermore, the treated material performed at least as well, overall, as the positive control lot used in these experiments.

Heat treating bad lots of poloxamer prior to use in cell culture media was an effective method of improving their cell protection performance. Heat treatment was effective at a wide range of temperatures and durations; however, the lower the temperature, the longer the necessary treatment time. This process was robust, demonstrating similar results across several poloxamer lots, and reproducible. While results presented here were from experiments conducted in an oven, the process can be transferred to larger scale equipment. The heat treatment process described herein can be transferred to any treatment method which will ensure consistent heating of poloxamer for a required duration at the necessary temperature.

Example 11: Statistical Analysis of DOE Test Data

The Examples described above demonstrate the effect of poloxamer heat treatment on subsequent performance in cell culture (e.g., cell viability). Next, analyses were undertaken to produce a transfer function, which is a mathematical model for the output (viability @ 3 hours in a shake flask model) as a function of the two dependent variables (Temperature and Time).

DOE Test data (described in Table 12) gathered in an oven with temperature and time as variables were analyzed in Minitab by Response Surface Regression method. A known bad lot of Poloxamer (G) was heat-treated per DOE test design and tested in a High Shear Shake Flask model used as a surrogate for shear protectant functionality. Higher viability at the end of the 3 hour test indicates better performance of poloxamer. Similarly, an evaluation between the same lot of poloxamer that has been treated to improve performance compared to an untreated sample (negative control) was performed. To account for intra lot variability observed in the poor performing lots, the average final viability of six G controls was used as baseline to calculate the percentage of viability improvements observed for each test case. Viability (%) at 3 hour and difference in treated vs untreated lots (%) were the response variables. The results show that quality of this poor performing lot can be improved as measured by increase in viability. The desired viability goal of positive change in viability (treated lot-untreated lot) can be achieved at various temperature and time treatments.

The analysis was performed with the change in viability (treated lot-untreated lot) @ 3 hrs. Since average final viability of one of the poor performing lot studied under stress conditions, G was found to be 79.7+/−5.0%, a 10% or 20% increase in viability was targeted for the contour plot and for establishing minimum duration of heat treatment at a designated temperature. It should also be noted that in case of another poor performer, C, lower viabilities (44.8+/−7.8%) than those seen for G may be expected for the untreated control. Therefore, >35% improvement in viabilities for C may be expected at conditions where a 20% augmentation was achieved for lot G. These results indicate that there exists linear effect of temperature and time, interaction of temperature and time. The terms in the models are statistically significant at 95% confidence level with P-value<0.05. The identification of the optimum operating range and the factors in the model are unexpected and novel findings.

TABLE 12

Data set for lot G heat treatment.

| Lot Number | Time, Min | Temperature, C. | Viability @ 3 hrs | Viability Improvement (over untreated control average) % |
|---|---|---|---|---|
| G | 1 | 110 | 74.9 | −4.77 |
| G | 5 | 140 | 77.05 | −2.62 |
| G | 10 | 170 | 88.9 | 9.23 |
| G | 30 | 185 | 89.5 | 9.83 |
| G | 60 | 155 | 88.65 | 8.98 |
| G | 120 | 125 | 82.25 | 2.58 |
| G | 10 | 140 | 91.3 | 11.63 |
| G | 1 | 155 | 93.6 | 13.93 |
| G | 30 | 140 | 95.5 | 15.83 |
| G | 120 | 185 | 95.85 | 16.18 |
| G | 1 | 185 | 93.9 | 14.23 |
| G | 5 | 155 | 92.6 | 12.93 |
| G | 10 | 125 | 73.4 | −6.27 |
| G | 30 | 110 | 51.9 | −27.77 |
| G | 60 | 140 | 93.7 | 14.03 |
| G | 120 | 170 | 82.6 | 2.93 |
| G | 60 | 110 | 82.1 | 2.43 |
| G | 120 | 140 | 95.9 | 16.23 |
| G | 1 | 140 | 68.5 | −11.17 |
| G | 5 | 170 | 94.5 | 14.83 |
| G | 10 | 185 | 95.6 | 15.93 |
| G | 30 | 155 | 95.2 | 15.53 |
| G | 60 | 125 | 68.15 | −11.52 |
| G | 120 | 110 | 94.75 | 15.08 |
| G | 1 | 140 | 91.5 | 11.83 |
| G | 30 | 140 | 89.5 | 9.83 |
| G | 30 | 140 | 90 | 10.33 |
| G | 1 | 155 | 90.8 | 11.13 |
| G | 1 | 155 | 90.7 | 11.03 |
| G | 30 | 155 | 89.5 | 9.83 |
| G | 1 | 170 | 90.6 | 10.93 |
| G | 30 | 170 | 89.4 | 9.73 |
| G | 120 | 60 | 77.2 | −2.47 |
| G | 120 | 80 | 74.7 | −4.97 |

HSSF model run in duplicates

For analysis software, Minitab version 17.1 (Minitab.com, State College Pa.) was used. Analysis was Regression analysis (RSRegress). Response surface regression was used to analyze viability improvement (over untreated lot) versus Time (min) and Temperature (° C.).

The analysis of variance, model summary, and coded coefficients are provided below in Tables 13-15.

TABLE 13

Analysis of Variance.

| Source | DF | Adj SS | Adj MS | F-Value | P-Value |
|---|---|---|---|---|---|
| Model | 5 | 1666.90 | 333.38 | 5.29 | 0.002 |
| Linear | 2 | 1369.54 | 684.77 | 10.87 | 0.000 |
| Time, min | 1 | 484.39 | 484.39 | 7.69 | 0.010 |
| Temp., ° C. | 1 | 1356.83 | 1356.83 | 21.54 | 0.000 |
| Square | 2 | 203.14 | 101.57 | 1.61 | 0.217 |
| (Time, min)$^2$ | 1 | 12.47 | 12.47 | 0.20 | 0.660 |
| (Temperature, C.)$^2$ | 1 | 201.47 | 201.47 | 3.20 | 0.085 |
| 2-Way Interaction | 1 | 432.89 | 432.89 | 6.87 | 0.014 |
| (Time, min)*(Temperature, C.) | 1 | 432.89 | 432.89 | 6.87 | 0.014 |
| Error | 28 | 1764.05 | 63.00 | | |
| Lack-of-Fit | 22 | 1455.72 | 66.17 | 1.29 | 0.403 |
| Pure Error | 6 | 308.33 | 51.39 | | |
| Total | 33 | 3430.94 | | | |

TABLE 14

Model Summary

| S | R-sq | R-sq(adj) | R-sq(pred) |
|---|---|---|---|
| 7.93736 | 48.58% | 39.40% | 8.41% |

TABLE 15

Coded Coefficients.

| Term | Effect | Coef. | SE Coef. | T-value | P-value | VIF |
|---|---|---|---|---|---|---|
| Constant | | 1.59 | 3.01 | 0.53 | 0.602 | |
| Time, min | 16.01 | 8.01 | 2.89 | 2.77 | 0.010 | 2.49 |
| Temp., ° C. | 41.89 | 20.94 | 4.51 | 4.64 | 0.000 | 2.31 |
| (Time, min)$^2$ | 3.32 | 1.66 | 3.73 | 0.44 | 0.660 | 1.08 |
| (Temperature, C.)$^2$ | −22.36 | −11.18 | 6.25 | −1.79 | 0.085 | 2.37 |
| (Time, min)*(Temperature, C.) | −24.78 | −12.39 | 4.73 | −2.62 | 0.014 | 2.22 |

Based on these results, a regression equation (in uncoded units) was determined as: Viability Improvement (over untreated lot),%=−113.5+0.486*(Time, min)+1.238*(Temperature, C)+0.00047*(Time, min)$^2$−0.00286*(Temperature, C)$^2$−0.00333*(Time, min)*(Temperature, C)

The transfer function shown above predicts the improvement in viability for lot G over untreated control as a function of heat treatment temperature and duration. It also contains second order terms involving temperature and time and their interaction. Using the above model, expected viability for a test case (not derived empricially) can be obtained. A sample output prediction is shown below for test conditions 157° C. and 1 minute:

Viability improvement=−113.5+(0.486*1)+(1.238*157)+0.00047*1^2)−(0.00286*157^2)−(0.00333*1*157)=10.3%

Figure 11:
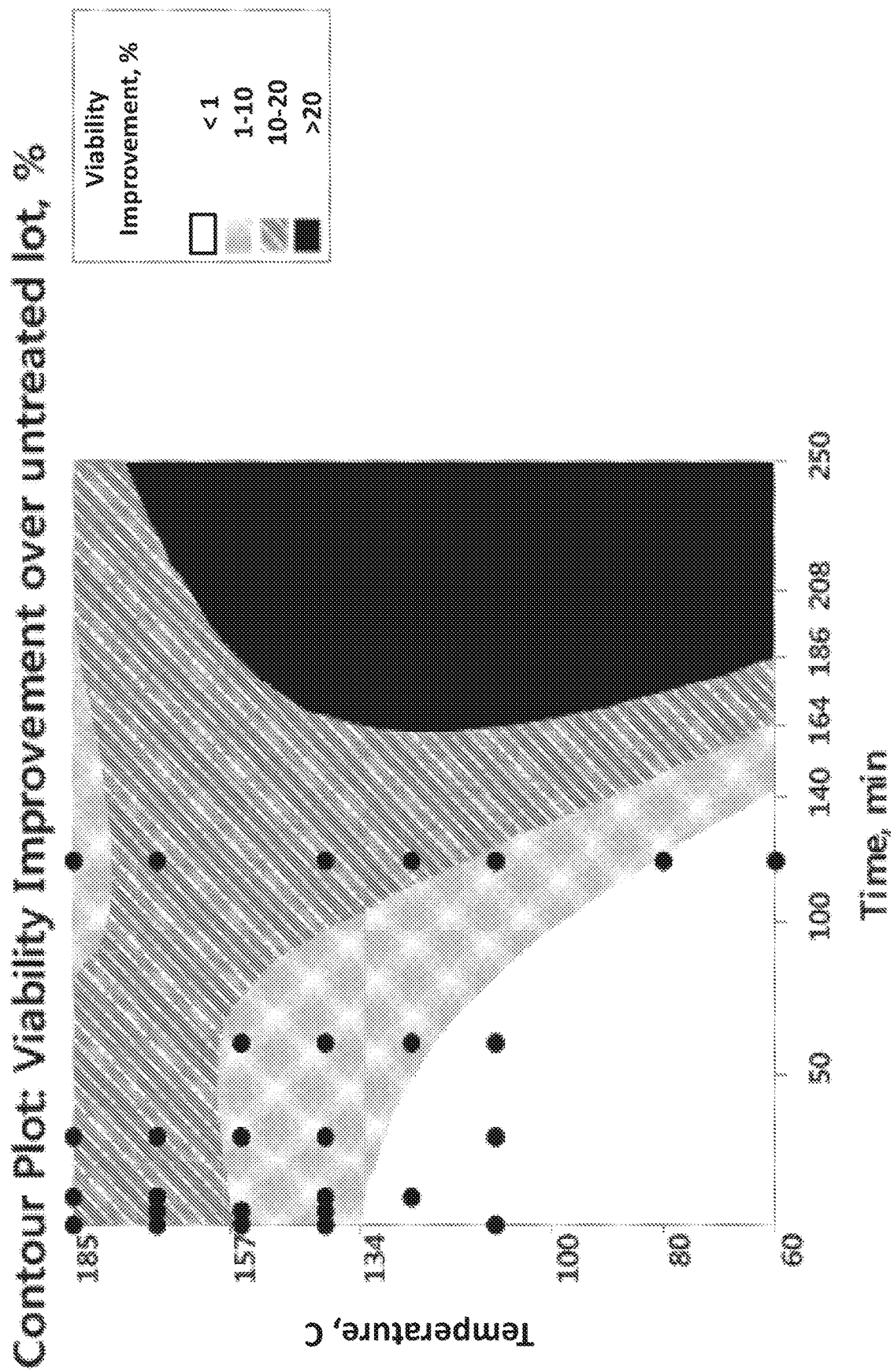
FIG. 11 shows a contour plot for data from response surface and full DOE experiments illustrating the large working range for poloxamer heat treatment conditions. Change in cell viability (%) for each experimental space is illustrated. Viability improvement ($Vf_{(treated)}-Vf_{(untreated)}$) in the HSSF test is shown as a function of time and temperature. Response surface data reflects incubation times and temperatures corrected for time required to reach target temperature. Dots indicate sample conditions tested.

The experimental data was used to generate the contour plot shown in FIG. 11 (empirical data shown in black circles). Based on the model generated by the regression, 5 points can be inferred mathematically.

First, the treatment response can be classified into three temperature zones (157° C.-185° C.). (134° C.-157° C.) and (60° C.-134° C.).

Second, in the high temperature zone of 157° C.-185° C., viabilities of heat treated lots can be improved from 1 to 20% within a minimum heat treatment of one minute.

Third, in the mid temperature zone of 134° C.-157° C., viabilities of heat treated lots can be improved between 1 and 10% within a minimum heat treatment duration of 1 minute.

Viabilities can be enhanced up to 20% with a minimum heat treatment duration of 120 minutes.

Fourth, in the low temperature zone of 60° C.-134° C., viabilities of heat treated lots can be improved up to 10% within a heat treatment duration of 140 minutes. Viabilities can be enhanced up to 20% with a minimum heat treatment duration of 164 minutes. It is to be noted that the durations described for the mid and low temperature zones are simplified guidelines. For example, as shown in FIG. 11, the temperatures of 60° C., 80° C., 120° C. within the low temperature zone require 164 minutes, 147 minutes, and 115 minutes, respectively, to achieve at least a 10% improvement in viability. Exemplary values are described in Table 16 below.

TABLE 16

Exemplary temperatures, times, and corresponding viability improvements.

| Temp Range, ° C. | Min Time required for light grey zone (1-10%) improvement, min | Min Time required for dark grey zone (10-20%) improvement, min | Min Time required for dark grey zone (>20%) improvement, min |
|---|---|---|---|
| 60 | 143 | 164 | 186 |
| 80 | 122 | 147 | 175 |
| 100 | 98 | 132 | 166 |
| 120 | 62 | 115 | 162 |
| 134 | 1 | 102 | 163 |
| 157 | 1 | 1 | NA |
| 185 | 1 | 1 | NA |

Fifth, the model set forth above was derived from data generated with lot G. Since the untreated control had a higher baseline viability of 79%, viability improvements can be realized to a maximum of 20%. However, for lots such as C, where the untreated lot had a much lower viability of 45%, higher levels of improvement can be realized. For example, in the mid temperature zone of 134° C.-157° C., viability can be improved by 42% within a heat treatment duration of 15 minutes for lot C. The observed differences in performance between lots C and G are summarized in Table 17 below.

TABLE 17

Summary of C and G performance

| | C | | G |
|---|---|---|---|
| Parameter | Sample Viability (%) @ 3 hr | Parameter | Sample Viability (%) @ 3 hr |
| Average | 44.8 | Average | 79.7 |
| Stdev | 7.4 | Stdev | 5.0 |
| N | 6 | N | 6 |

Therefore, the heat treatment value is more pronounced in lots such as C. A full data set for this lot could not be performed due to lack of raw material to run a full set of experiments. G represents a marginally poor performing lot and the model predicted above can be considered conservative. The data generated using lots C and G demonstrate that heat-treating poloxamer may improve the performance of other poloxamer lots not tested here. The improvements in performance may be affected by time and temperature as described above. The results described above demonstrate that increasing temperature shortens the duration of heat treatment required to improve poloxamer performance, and that lower temperatures may be used to improve poloxamer performance over longer durations. Without wishing to be bound to theory, it is thought that the precise percentage of viability improvement observed upon heat treatment will depend upon the baseline viability observed for a particular poloxamer lot before heat treatment.

What is claimed is:

1. A method of producing a polypeptide in a cell culture, comprising the step of culturing a cell that produces the polypeptide in a cell culture medium under conditions suitable for production of the polypeptide, wherein the cell culture medium comprises a poloxamer prepared by a method comprising:
    (a) heating a solid poloxamer to form a liquid poloxamer, wherein the solid poloxamer is heated to:
        (1) between 157° C. and 185° C. for at least 1 minute,
        (2) between 134° C. and 157° C. for at least 1 minute,
        (3) between 120° C. and 134° C. for at least 62 minutes,
        (4) between 100° C. and 120° C. for at least 98 minutes,
        (5) between 80° C. and 100° C. for at least 122 minutes, or
        (6) between 60° C. and 80° C. for at least 143 minutes; and
    (b) cooling the liquid poloxamer to a temperature below 50° C. to form a solid heat-treated poloxamer, wherein the cooling is not conducted in a prilling or milling device, wherein the poloxamer comprises a copolymer of ethylene oxide and propylene oxide; and
wherein the poloxamer comprises a copolymer having a formula of $HO(C_2H_4O)_n(C_3H_6O)_m(C_2H_4O)_nH$ with n having a value of 80, with m having a value of 27, and the poloxamer has an average molecular weight of from 7680 to 9510 g/mol.

2. The method of claim 1, wherein the cell is a mammalian cell.

3. The method of claim 1, wherein the cell is a Chinese Hamster Ovary (CHO) cell.

4. The method of claim 1, wherein the cell is an insect cell.

5. The method of claim 1, wherein the cell medium comprises the heat-treated poloxamer at about 0.1 g/L to about 10 g/L.

6. The method of claim 5, wherein the cell medium comprises the heat-treated poloxamer at about 0.1 g/L to about 3 g/L.

7. The method of claim 5, wherein the cell medium comprises the heat-treated poloxamer at about 3 g/L to about 10 g/L.

8. The method of claim 1, wherein the polypeptide is an antibody or antigen-binding fragment thereof.

9. The method of claim 1, wherein the liquid poloxamer in step (b) is cooled at ambient temperature, 2° C. to 8° C., or below 0° C.

10. The method of claim 1, wherein the poloxamer is heated under a vacuum.

11. The method of claim 1, wherein the liquid poloxamer is cooled for at least 20 minutes.

12. The method of claim 1, wherein the poloxamer has been treated by a prilling process before step (a).

13. The method of claim 1, wherein the poloxamer is poloxamer 188.

\* \* \* \* \*